US008858958B2

(12) United States Patent
Pallaoro et al.

(10) Patent No.: US 8,858,958 B2
(45) Date of Patent: Oct. 14, 2014

(54) ADJUVANT COMPRISING ALUMINUM, OLIGONUCLEOTIDE AND POLYCATION

(75) Inventors: Michele Pallaoro, Siena (IT); Derek O'Hagan, Cambridge, MA (US); Rino Rappuoli, Castelnuovo Berardenga (IT)

(73) Assignee: Novartis AG, Basel (CH)

( * ) Notice: Subject to any disclaimer, the term of this patent is extended or adjusted under 35 U.S.C. 154(b) by 127 days.

(21) Appl. No.: 12/870,708

(22) Filed: Aug. 27, 2010

(65) Prior Publication Data

US 2011/0052716 A1    Mar. 3, 2011

Related U.S. Application Data

(60) Provisional application No. 61/237,595, filed on Aug. 27, 2009.

(51) Int. Cl.
| | | |
|---|---|---|
| *A61K 39/095* | (2006.01) | |
| *A61K 39/39* | (2006.01) | |
| *A61K 39/00* | (2006.01) | |
| *A61K 39/108* | (2006.01) | |
| *A61K 39/085* | (2006.01) | |
| *A61K 39/09* | (2006.01) | |
| *A61K 39/155* | (2006.01) | |

(52) U.S. Cl.
CPC ............. *A61K 39/39* (2013.01); *A61K 39/0002* (2013.01); *A61K 39/0258* (2013.01); *A61K 39/085* (2013.01); *A61K 39/092* (2013.01); *A61K 39/095* (2013.01); *A61K 39/155* (2013.01); *A61K 2039/55505* (2013.01); *A61K 2039/55555* (2013.01); *A61K 2039/55561* (2013.01); *C12N 2760/18534* (2013.01)
USPC .................. 424/249.1; 424/250.1; 424/278.1; 424/282.1; 436/86

(58) Field of Classification Search
USPC ......... 424/249.1, 250.1, 278.1, 282.1; 436/86
See application file for complete search history.

(56) References Cited

U.S. PATENT DOCUMENTS

| | | | | |
|---|---|---|---|---|
| 6,165,774 | A * | 12/2000 | Cates et al. .................. | 435/238 |
| 6,869,607 | B1 | 3/2005 | Buschle et al. | |
| 7,105,162 | B1 | 9/2006 | Schmidt et al. | |
| 2006/0263386 | A1 * | 11/2006 | Buschle et al. ............ | 424/204.1 |

FOREIGN PATENT DOCUMENTS

| | | |
|---|---|---|
| WO | 03/009869 A1 | 2/2003 |
| WO | 2004/084937 A1 | 10/2004 |
| WO | 2004/084938 A1 | 10/2004 |
| WO | 2007/071786 A2 | 6/2007 |
| WO | 2009/077854 A2 | 6/2009 |
| WO | 2009/104097 A2 | 8/2009 |

OTHER PUBLICATIONS

Schellack et al., IC31, a Novel Adjuvant Signaling via TLR9, Induces Potent Cellular and Humoral Immune Responses, Apr. 7, 2006, Vaccine, vol. 24, pp. 5461-5472. (See IDS submission).*
Alving and Matyas (2005) "Design and selection of vaccine adjuvants: principles and practice," in *The Grand Challenge for the Future: Vaccines for the Poverty-Related Disease from Bench to Field*, Kaufmann and Lambert, pp. 99-108.
Dekker et al. (2008) "Dose Optimization Strategies for Vaccines: The Role of Adjuvants and New Technologies," Feb. 2008 NVAC Meeting, 21 pages.
Edelman (2002). "The development and use of vaccine adjuvants," Molecular Biotechnology 21(2):129-148.
Gupta et al.. "Adjuvant Properties of Aluminum and Calcium Compounds", Pharmaceutical Biotechnology, 6: 229-248 (1995).
Riedl et al., "The novel adjuvant IC31(R) strongly improves influenza vaccine-specific cellular and humoral immune responses in young adult and aged mice", Vaccine, 26(27-28): 3461-3468 (2008).
Guiliani et al., "A universal vaccine for serogroup B meningococcus", Proc. Natl. Acad. Sci. USA, 103(29): 10834-10839 (2006).
Agger et al., "Protective immunity to tuberculosis with Ag85B-ESAT-6 in a synthetic cationic adjuvant system IC31", Vaccine, 24(26): 5452-5460 (2006).
Kamath et al., "Protective anti-mycobacterial T cell responses through exquisite in vivo activation of vaccine-targeted dendritic cells", Eur. J. Immunol., 38: 1247-1256 2008).
Lingnau et al., "IC31® and IC30, novel types of vaccine adjuvant based on peptide delivery systems", Expert Rev. Vaccines, 6(6): 741-746 (2007).
Fritz et al., "The artificial antimicrobial peptide KLKLLLLLKLK induces predominantly a TH2-type immune response to co-injected antigens", Vaccine, 22: 3274-3284 (2004).
Nakajima et al., "Chemotherapeutic activity of synthetic antimicrobial peptides: correlation between chemotherapeutic activity and neutrophil-activating activity", FEBS Letts., 415(1): 64-66 (1997).
Aichinger et al., "Unique membrane-interacting properties of the immunostimulatory cationic peptide KLKL5KLK (KLK)", Cell Biology International, 32(11): 1449-1458 (2008).
Alvarez-Bravo et al., "Novel synthetic antimicrobial peptides effective against methicillin-resistant *Staphylococcus aureus*", Biochem. J., 302: 535-538 (1994).

* cited by examiner

*Primary Examiner* — Ali Soroush
(74) *Attorney, Agent, or Firm* — Helen Lee; Otis Littlefield

(57) ABSTRACT

An immunological adjuvant comprises an aluminum salt, an immunostimulatory oligonucleotide and a polycationic polymer, wherein the oligonucleotide and the polymer ideally associate with each other to form a complex. The adjuvant can be included in a composition with an immunogen e.g. to elicit an immune response that protects against a bacterial disease or a fungal disease.

18 Claims, No Drawings

SEQUENCE LISTING

```
<160> NUMBER OF SEQ ID NOS: 26

<210> SEQ ID NO 1
<211> LENGTH: 26
<212> TYPE: DNA
<213> ORGANISM: Artificial Sequence
<220> FEATURE:
<223> OTHER INFORMATION: immunostimulatory oligonucleotide
<220> FEATURE:
<221> NAME/KEY: misc_feature
<222> LOCATION: 1, 3, 5, 7, 9, 11, 13, 15, 17, 19, 21, 23, 25
<223> OTHER INFORMATION: 'n' is INOSINE

<400> SEQUENCE: 1
ncncncncnc ncncncncnc ncncnc                                          26

<210> SEQ ID NO 2
<211> LENGTH: 11
<212> TYPE: PRT
<213> ORGANISM: Artificial Sequence
<220> FEATURE:
<223> OTHER INFORMATION: polycationic oligopeptide

<400> SEQUENCE: 2

Lys Leu Lys Leu Leu Leu Leu Leu Lys Leu Lys
1               5                   10

<210> SEQ ID NO 3
<211> LENGTH: 488
<212> TYPE: PRT
<213> ORGANISM: Neisseria meningitidis

<400> SEQUENCE: 3

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125
```

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 4
<211> LENGTH: 364
<212> TYPE: PRT
<213> ORGANISM: Neisseria meningitidis

<400> SEQUENCE: 4

Met Ser Met Lys His Phe Pro Ser Lys Val Leu Thr Thr Ala Ile Leu
1               5                   10                  15

```
Ala Thr Phe Cys Ser Gly Ala Leu Ala Ala Thr Ser Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Thr Ile Tyr Asp Ile Gly Glu
    50                  55                  60

Asp Gly Thr Ile Thr Gln Lys Asp Ala Thr Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
        130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
            195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 5
<211> LENGTH: 174
<212> TYPE: PRT
<213> ORGANISM: Neisseria meningitidis

<400> SEQUENCE: 5

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
```

```
            20                  25                  30
His Ala Lys Ala Ser Ser Leu Gly Ser Lys Gly Phe Ser Pro
            35                  40                  45

Arg Ile Ser Ala Gly Tyr Arg Ile Asn Asp Leu Arg Phe Ala Val Asp
50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
            115                 120                 125

Val Leu Thr Gly Val Ser Tyr Ala Val Thr Pro Asn Val Asp Leu Asp
            130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 6
<211> LENGTH: 591
<212> TYPE: PRT
<213> ORGANISM: Neisseria meningitidis

<400> SEQUENCE: 6

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
            130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
            210                 215                 220
```

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
            245                 250                 255

Thr Thr Val Asn Val Glu Ser Lys Asp Asn Gly Lys Lys Thr Glu Val
        260                 265                 270

Lys Ile Gly Ala Lys Thr Ser Val Ile Lys Glu Lys Asp Gly Lys Leu
    275                 280                 285

Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
            325                 330                 335

Asp Lys Phe Glu Thr Val Thr Ser Gly Thr Asn Val Thr Phe Ala Ser
        340                 345                 350

Gly Lys Gly Thr Thr Ala Thr Val Ser Lys Asp Gln Gly Asn Ile
    355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
        420                 425                 430

Asn Gly Lys Asn Ile Asp Ile Ala Thr Ser Met Thr Pro Gln Phe Ser
    435                 440                 445

Ser Val Ser Leu Gly Ala Gly Ala Asp Ala Pro Thr Leu Ser Val Asp
450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
            485                 490                 495

Ala Gln Leu Lys Gly Val Ala Gln Asn Leu Asn Asn Arg Ile Asp Asn
        500                 505                 510

Val Asp Gly Asn Ala Arg Ala Gly Ile Ala Gln Ala Ile Ala Thr Ala
    515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
        580                 585                 590

<210> SEQ ID NO 7
<211> LENGTH: 1457
<212> TYPE: PRT
<213> ORGANISM: Neisseria meningitidis

<400> SEQUENCE: 7

Met Lys Thr Thr Asp Lys Arg Thr Thr Glu Thr His Arg Lys Ala Pro
1               5                   10                  15

```
Lys Thr Gly Arg Ile Arg Phe Ser Pro Ala Tyr Leu Ala Ile Cys Leu
             20                  25                  30

Ser Phe Gly Ile Leu Pro Gln Ala Trp Ala Gly His Thr Tyr Phe Gly
         35                  40                  45

Ile Asn Tyr Gln Tyr Tyr Arg Asp Phe Ala Glu Asn Lys Gly Lys Phe
     50                  55                  60

Ala Val Gly Ala Lys Asp Ile Glu Val Tyr Asn Lys Lys Gly Glu Leu
 65              70                  75                  80

Val Gly Lys Ser Met Thr Lys Ala Pro Met Ile Asp Phe Ser Val Val
                 85                  90                  95

Ser Arg Asn Gly Val Ala Ala Leu Val Gly Asp Gln Tyr Ile Val Ser
                100                 105                 110

Val Ala His Asn Gly Gly Tyr Asn Asn Val Asp Phe Gly Ala Glu Gly
             115                 120                 125

Arg Asn Pro Asp Gln His Arg Phe Thr Tyr Lys Ile Val Lys Arg Asn
         130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                 165                 170                 175

Thr Ser Tyr Met Asp Gly Arg Lys Tyr Ile Asp Gln Asn Asn Tyr Pro
                180                 185                 190

Asp Arg Val Arg Ile Gly Ala Gly Arg Gln Tyr Trp Arg Ser Asp Glu
             195                 200                 205

Asp Glu Pro Asn Asn Arg Glu Ser Ser Tyr His Ile Ala Ser Ala Tyr
         210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                 245                 250                 255

Phe Leu Pro Thr Gly Gly Ser Phe Gly Asp Ser Gly Ser Pro Met Phe
             260                 265                 270

Ile Tyr Asp Ala Gln Lys Gln Lys Trp Leu Ile Asn Gly Val Leu Gln
         275                 280                 285

Thr Gly Asn Pro Tyr Ile Gly Lys Ser Asn Gly Phe Gln Leu Val Arg
     290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                 325                 330                 335

Asn Gly Thr Gly Lys Ile Asn Ala Lys His Glu His Asn Ser Leu Pro
             340                 345                 350

Asn Arg Leu Lys Thr Arg Thr Val Gln Leu Phe Asn Val Ser Leu Ser
         355                 360                 365

Glu Thr Ala Arg Glu Pro Val Tyr His Ala Ala Gly Gly Val Asn Ser
     370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                 405                 410                 415

Gly Leu Tyr Phe Gln Gly Asp Phe Thr Val Ser Pro Glu Asn Asn Glu
             420                 425                 430
```

```
Thr Trp Gln Gly Ala Gly Val His Ile Ser Glu Asp Ser Thr Val Thr
            435                 440                 445

Trp Lys Val Asn Gly Val Ala Asn Asp Arg Leu Ser Lys Ile Gly Lys
450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Lys Gly
                485                 490                 495

Lys Lys Gln Ala Phe Ser Glu Ile Gly Leu Val Ser Arg Gly Thr
            500                 505                 510

Val Gln Leu Asn Ala Asp Asn Gln Phe Asn Pro Asp Lys Leu Tyr Phe
            515                 520                 525

Gly Phe Arg Gly Gly Arg Leu Asp Leu Asn Gly His Ser Leu Ser Phe
530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
            595                 600                 605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
            675                 680                 685

Gly Gly Gln Ala Val Val Ser Arg Asn Val Ala Lys Val Lys Gly Asp
690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Lys Val Ile Ala Ser Leu Thr
                740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
```

```
            850                 855                 860
Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                    900                 905                 910

Asn Ser Ala Tyr Arg His Asp Ala Ala Gly Gln Thr Gly Ser Ala
                915                 920                 925

Thr Asp Ala Pro Arg Arg Ser Arg Arg Ser Arg Ser Leu Leu
        930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                    965                 970                 975

Leu Phe Gly Tyr Arg Ser Asp Lys Leu Lys Leu Ala Glu Ser Ser Glu
                980                 985                 990

Gly Thr Tyr Thr Leu Ala Val Asn Asn Thr Gly Asn Glu Pro Ala Ser
                995                 1000                1005

Leu Glu Gln Leu Thr Val Val Glu Gly Lys Asp Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
                1060                1065                1070

Lys Lys Gln Ala Glu Lys Asp Asn Ala Gln Ser Leu Asp Ala Leu Ile
            1075                1080                1085

Ala Ala Gly Arg Asp Ala Val Glu Lys Thr Glu Ser Val Ala Glu Pro
        1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
                1140                1145                1150

Arg Ala Arg Arg Asp Leu Pro Gln Leu Gln Pro Gln Pro Gln
            1155                1160                1165

Pro Gln Arg Asp Leu Ile Ser Arg Tyr Ala Asn Ser Gly Leu Ser Glu
    1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
                1205                1210                1215

Arg Asp Thr Lys His Tyr Arg Ser Gln Asp Phe Arg Ala Tyr Arg Gln
                1220                1225                1230

Gln Thr Asp Leu Arg Gln Ile Gly Met Gln Lys Asn Leu Gly Ser Gly
            1235                1240                1245

Arg Val Gly Ile Leu Phe Ser His Asn Arg Thr Glu Asn Thr Phe Asp
    1250                1255                1260

Asp Gly Ile Gly Asn Ser Ala Arg Leu Ala His Gly Ala Val Phe Gly
1265                1270                1275                1280
```

```
Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Lys Ile Arg Arg
        1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
            1380                1385                1390

Asp Ala Ala Ser Gly Lys Val Arg Thr Arg Val Asn Thr Ala Val Leu
            1395                1400                1405

Ala Gln Asp Phe Gly Lys Thr Arg Ser Ala Glu Trp Gly Val Asn Ala
        1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
            1445                1450                1455

Trp

<210> SEQ ID NO 8
<211> LENGTH: 797
<212> TYPE: PRT
<213> ORGANISM: Neisseria meningitidis

<400> SEQUENCE: 8

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Arg Lys Leu
            180                 185                 190
```

```
Met Arg Gln Met Ser Leu Thr Glu Gly Gly Ile Trp Thr Trp Leu Thr
            195                 200                 205

Arg Ser Asn Gln Phe Asn Glu Gln Lys Phe Ala Gln Asp Met Glu Lys
        210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
                260                 265                 270

Glu Gly Asp Thr Asn Glu Val Pro Lys Ala Glu Leu Glu Lys Leu Leu
            275                 280                 285

Thr Met Lys Pro Gly Lys Trp Tyr Glu Arg Gln Gln Met Thr Ala Val
        290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
                340                 345                 350

His Ile Thr Gly Asn Asn Lys Thr Arg Asp Glu Val Val Arg Arg Glu
            355                 360                 365

Leu Arg Gln Met Glu Ser Ala Pro Tyr Asp Thr Ser Lys Leu Gln Arg
        370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
                420                 425                 430

Val Gln Asp Thr Gly Leu Val Met Ser Ala Gly Val Ser Gln Asp Asn
            435                 440                 445

Leu Phe Gly Thr Gly Lys Ser Ala Ala Leu Arg Ala Ser Arg Ser Lys
        450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Thr Ala Gly
                500                 505                 510

Ala Gly Ile Arg Met Ser Val Pro Val Thr Glu Tyr Asp Arg Val Asn
            515                 520                 525

Phe Gly Leu Val Ala Glu His Leu Thr Val Asn Thr Tyr Asn Lys Ala
        530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
                580                 585                 590

Thr Gly Val Asn Ala Glu Ile Ala Leu Pro Gly Ser Lys Leu Gln Tyr
            595                 600                 605
```

Tyr Ser Ala Thr His Asn Gln Thr Trp Phe Phe Pro Leu Ser Lys Thr
610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
                660                 665                 670

Asp Glu Tyr Gly Glu Lys Ile Ser Tyr Gly Gly Asn Lys Lys Ala Asn
                675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
                740                 745                 750

Leu Arg Tyr Ser Ala Gly Gly Ala Val Thr Trp Leu Ser Pro Leu Gly
                755                 760                 765

Pro Met Lys Phe Ser Tyr Ala Tyr Pro Leu Lys Lys Pro Glu Asp
770                 775                 780

Glu Ile Gln Arg Phe Gln Phe Gln Leu Gly Thr Thr Phe
785                 790                 795

<210> SEQ ID NO 9
<211> LENGTH: 248
<212> TYPE: PRT
<213> ORGANISM: Neisseria meningitidis

<400> SEQUENCE: 9

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
            245

<210> SEQ ID NO 10
<211> LENGTH: 247
<212> TYPE: PRT
<213> ORGANISM: Neisseria meningitidis

<400> SEQUENCE: 10

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
            85                  90                  95

Ser Ala Val Val Ala Leu Gln Ile Glu Lys Ile Asn Asn Pro Asp Lys
        100                 105                 110

Ile Asp Ser Leu Ile Asn Gln Arg Ser Phe Leu Val Ser Gly Leu Gly
    115                 120                 125

Gly Glu His Thr Ala Phe Asn Gln Leu Pro Asp Gly Lys Ala Glu Tyr
130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
            165                 170                 175

Lys Thr Pro Glu Gln Asn Val Glu Leu Ala Ala Ala Glu Leu Lys Ala
        180                 185                 190

Asp Glu Lys Ser His Ala Val Ile Leu Gly Asp Thr Arg Tyr Gly Ser
    195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln
            245

<210> SEQ ID NO 11
<211> LENGTH: 250
<212> TYPE: PRT
<213> ORGANISM: Neisseria meningitidis

<400> SEQUENCE: 11

Val Ala Ala Asp Ile Gly Thr Gly Leu Ala Asp Ala Leu Thr Ala Pro
1               5                   10                  15

```
Leu Asp His Lys Asp Lys Gly Leu Lys Ser Leu Thr Leu Glu Asp Ser
             20                  25                  30

Ile Pro Gln Asn Gly Thr Leu Thr Leu Ser Ala Gln Gly Ala Glu Lys
         35                  40                  45

Thr Phe Lys Ala Gly Asp Lys Asp Asn Ser Leu Asn Thr Gly Lys Leu
 50                  55                  60

Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                 85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
130                 135                 140

Ala Glu Tyr His Gly Lys Ala Phe Ser Ser Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 12
<211> LENGTH: 792
<212> TYPE: PRT
<213> ORGANISM: Neisseria meningitidis

<400> SEQUENCE: 12

Met Lys Pro Leu Gln Met Leu Pro Ile Ala Ala Leu Val Gly Ser Ile
 1                   5                  10                  15

Phe Gly Asn Pro Val Leu Ala Ala Asp Glu Ala Ala Thr Glu Thr Thr
             20                  25                  30

Pro Val Lys Ala Glu Ile Lys Ala Val Arg Val Lys Gly Gln Arg Asn
         35                  40                  45

Ala Pro Ala Ala Val Glu Arg Val Asn Leu Asn Arg Ile Lys Gln Glu
 50                  55                  60

Met Ile Arg Asp Asn Lys Asp Leu Val Arg Tyr Ser Thr Asp Val Gly
 65                  70                  75                  80

Leu Ser Asp Ser Gly Arg His Gln Lys Gly Phe Ala Val Arg Gly Val
                 85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
```

```
            130                 135                 140
Gly Ala Asp Ser Phe Asn Thr Gly Ser Gly Ala Leu Gly Gly Val
145                 150                 155                 160

Asn Tyr Gln Thr Leu Gln Gly Arg Asp Leu Leu Asp Asp Arg Gln
            165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
        210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
                260                 265                 270

Ala Ser Leu Asn Gly Gln Gln Gly His Asn Tyr Thr Val Glu Glu Ser
            275                 280                 285

Tyr Asn Leu Thr Ala Ser Ser Trp Arg Glu Ala Asp Asp Val Asn Arg
        290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
                325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
        355                 360                 365

Asp Thr Arg Phe Lys Arg Phe Thr Leu Arg Leu Asp Ser His Pro Leu
370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
                405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
        435                 440                 445

Ser Ser Arg Ala Gly Ile Arg Tyr Asp His Thr Lys Met Thr Pro Gln
450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                485                 490                 495

Asn Gln Ala Trp Arg Val Gly Tyr Asp Ile Thr Ser Gly Tyr Arg Val
            500                 505                 510

Pro Asn Ala Ser Glu Val Tyr Phe Thr Tyr Asn His Gly Ser Gly Asn
        515                 520                 525

Trp Leu Pro Asn Pro Asn Leu Lys Ala Glu Arg Ser Thr Thr His Thr
530                 535                 540

Leu Ser Leu Gln Gly Arg Ser Glu Lys Gly Met Leu Asp Ala Asn Leu
545                 550                 555                 560
```

Tyr Gln Ser Asn Tyr Arg Asn Phe Leu Ser Glu Gln Lys Leu Thr
                565                 570                 575

Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
        595                 600                 605

Asp Lys Ala Arg Ile Arg Gly Ile Glu Leu Thr Gly Arg Leu Asn Val
610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
        755                 760                 765

Arg Asp Gly Lys Gly Leu Asp Arg Tyr Arg Ala Pro Gly Arg Asn Tyr
770                 775                 780

Ala Val Ser Leu Glu Trp Lys Phe
785                 790

<210> SEQ ID NO 13
<211> LENGTH: 644
<212> TYPE: PRT
<213> ORGANISM: Neisseria meningitidis

<400> SEQUENCE: 13

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
        50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly

```
                130               135               140
Asn Thr Ala Ala Gln Gly Thr Asn Gln Ala Glu Asn Asn Gln Thr Ala
145                 150               155                 160

Gly Ser Gln Asn Pro Ala Ser Ser Thr Asn Pro Ser Ala Thr Asn Ser
                165               170               175

Gly Gly Asp Phe Gly Arg Thr Asn Val Gly Asn Ser Val Val Ile Asp
                180               185               190

Gly Pro Ser Gln Asn Ile Thr Leu Thr His Cys Lys Gly Asp Ser Cys
                195               200               205

Ser Gly Asn Asn Phe Leu Asp Glu Glu Val Gln Leu Lys Ser Glu Phe
                210               215               220

Glu Lys Leu Ser Asp Ala Asp Lys Ile Ser Asn Tyr Lys Lys Asp Gly
225                 230               235                 240

Lys Asn Asp Gly Lys Asn Asp Lys Phe Val Gly Leu Val Ala Asp Ser
                245               250               255

Val Gln Met Lys Gly Ile Asn Gln Tyr Ile Ile Phe Tyr Lys Pro Lys
                260               265               270

Pro Thr Ser Phe Ala Arg Phe Arg Arg Ser Ala Arg Ser Arg Arg Ser
                275               280               285

Leu Pro Ala Glu Met Pro Leu Ile Pro Val Asn Gln Ala Asp Thr Leu
                290               295               300

Ile Val Asp Gly Glu Ala Val Ser Leu Thr Gly His Ser Gly Asn Ile
305                 310               315                 320

Phe Ala Pro Glu Gly Asn Tyr Arg Tyr Leu Thr Tyr Gly Ala Glu Lys
                325               330               335

Leu Pro Gly Gly Ser Tyr Ala Leu Arg Val Gln Gly Glu Pro Ser Lys
                340               345               350

Gly Glu Met Leu Ala Gly Thr Ala Val Tyr Asn Gly Glu Val Leu His
                355               360               365

Phe His Thr Glu Asn Gly Arg Pro Ser Pro Ser Arg Gly Arg Phe Ala
                370               375               380

Ala Lys Val Asp Phe Gly Ser Lys Ser Val Asp Gly Ile Ile Asp Ser
385                 390               395                 400

Gly Asp Gly Leu His Met Gly Thr Gln Lys Phe Lys Ala Ala Ile Asp
                405               410               415

Gly Asn Gly Phe Lys Gly Thr Trp Thr Glu Asn Gly Gly Asp Val
                420               425               430

Ser Gly Lys Phe Tyr Gly Pro Ala Gly Glu Glu Val Ala Gly Lys Tyr
                435               440               445

Ser Tyr Arg Pro Thr Asp Ala Glu Lys Gly Gly Phe Gly Val Phe Ala
450                 455               460

Gly Lys Lys Glu Gln Asp Gly Ser Gly Gly Gly Ala Thr Tyr Lys
465                 470               475                 480

Val Asp Glu Tyr His Ala Asn Ala Arg Phe Ala Ile Asp His Phe Asn
                485               490               495

Thr Ser Thr Asn Val Gly Gly Phe Tyr Gly Leu Thr Gly Ser Val Glu
                500               505               510

Phe Asp Gln Ala Lys Arg Asp Gly Lys Ile Asp Ile Thr Ile Pro Val
                515               520               525

Ala Asn Leu Gln Ser Gly Ser Gln His Phe Thr Asp His Leu Lys Ser
                530               535               540

Ala Asp Ile Phe Asp Ala Ala Gln Tyr Pro Asp Ile Arg Phe Val Ser
545                 550               555                 560
```

```
Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640

Ala Ala Lys Gln

<210> SEQ ID NO 14
<211> LENGTH: 434
<212> TYPE: PRT
<213> ORGANISM: Neisseria meningitidis

<400> SEQUENCE: 14

Met Val Ser Ala Val Ile Gly Ser Ala Ala Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
        50                  55                  60

Leu Leu Leu Leu Gly Gln Val Ala Thr Glu Gly Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285
```

```
Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                    325                 330                 335

Gly Ser Asp Asp Ala Gly Gly Lys Leu Thr Tyr Thr Ile Asp Phe Ala
                340                 345                 350

Ala Lys Gln Gly Asn Gly Lys Ile Glu His Leu Lys Ser Pro Glu Leu
            355                 360                 365

Asn Val Asp Leu Ala Ala Asp Ile Lys Pro Asp Gly Lys Arg His
370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln
```

<210> SEQ ID NO 15
<211> LENGTH: 350
<212> TYPE: PRT
<213> ORGANISM: Neisseria meningitidis

<400> SEQUENCE: 15

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
            35                  40                  45

Asn Gly Phe Lys Ala Gly Glu Thr Ile Tyr Asp Ile Asp Glu Asp Gly
50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220
```

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
            245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
            290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
            325                 330                 335

Gln Ala Ala Leu Ser Gly Leu Phe Gln Pro Tyr Asn Val Gly
            340                 345                 350

<210> SEQ ID NO 16
<211> LENGTH: 249
<212> TYPE: PRT
<213> ORGANISM: Neisseria meningitidis

<400> SEQUENCE: 16

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
            35                  40                  45

Lys Thr Tyr Gly Asn Gly Asp Ser Leu Asn Thr Gly Lys Leu Lys Asn
50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
            85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
            115                 120                 125

Ala Gly Glu His Thr Ser Phe Asp Lys Leu Pro Glu Gly Gly Arg Ala
            130                 135                 140

Thr Tyr His Gly Lys Ala Phe Gly Ser Asp Asp Pro Asn Gly Arg Leu
145                 150                 155                 160

His Tyr Thr Ile Asp Phe Ala Ala Lys Gln Gly Tyr Gly Arg Ile Glu
            165                 170                 175

His Leu Lys Thr Pro Glu Gln Asn Val Asp Leu Ala Ala Ala Asp Ile
            180                 185                 190

Lys Pro Asp Gly Lys Arg His Ala Val Ile Ser Gly Ser Val Leu Tyr
            195                 200                 205

Asn Gln Ala Glu Lys Gly Ser Tyr Ser Leu Gly Ile Phe Gly Gly Lys
            210                 215                 220

Ala Gln Glu Val Ala Gly Ser Ala Glu Val Lys Ile Gly Glu Gly Ile
225                 230                 235                 240

Arg His Ile Gly Leu Ala Ala Lys Gln

245

<210> SEQ ID NO 17
<211> LENGTH: 776
<212> TYPE: PRT
<213> ORGANISM: Neisseria meningitidis

<400> SEQUENCE: 17

```
Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Pro Asp Ser Asp Arg Leu Gln Gln Arg Arg
            260                 265                 270

Val Ala Ala Asp Ile Gly Thr Gly Leu Ala Asp Ala Leu Thr Ala Pro
        275                 280                 285

Leu Asp His Lys Asp Lys Gly Leu Lys Ser Leu Thr Leu Glu Asp Ser
    290                 295                 300

Ile Pro Gln Asn Gly Thr Leu Thr Leu Ser Ala Gln Gly Ala Glu Lys
305                 310                 315                 320

Thr Phe Lys Ala Gly Asp Lys Asp Asn Ser Leu Asn Thr Gly Lys Leu
                325                 330                 335

Lys Asn Asp Lys Ile Ser Arg Phe Asp Phe Val Gln Lys Ile Glu Val
            340                 345                 350

Asp Gly Gln Thr Ile Thr Leu Ala Ser Gly Glu Phe Gln Ile Tyr Lys
        355                 360                 365
```

-continued

```
Gln Asn His Ser Ala Val Val Ala Leu Gln Ile Glu Lys Ile Asn Asn
    370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                    405                 410                 415

Ala Glu Tyr His Gly Lys Ala Phe Ser Ser Asp Asp Pro Asn Gly Arg
                420                 425                 430

Leu His Tyr Ser Ile Asp Phe Thr Lys Lys Gln Gly Tyr Gly Arg Ile
            435                 440                 445

Glu His Leu Lys Thr Leu Glu Gln Asn Val Glu Leu Ala Ala Ala Glu
    450                 455                 460

Leu Lys Ala Asp Glu Lys Ser His Ala Val Ile Leu Gly Asp Thr Arg
465                 470                 475                 480

Tyr Gly Ser Glu Glu Lys Gly Thr Tyr His Leu Ala Leu Phe Gly Asp
                    485                 490                 495

Arg Ala Gln Glu Ile Ala Gly Ser Ala Thr Val Lys Ile Gly Glu Lys
                500                 505                 510

Val His Glu Ile Gly Ile Ala Gly Lys Gln Gly Ser Gly Gly Gly
            515                 520                 525

Val Ala Ala Asp Ile Gly Ala Gly Leu Ala Asp Ala Leu Thr Ala Pro
    530                 535                 540

Leu Asp His Lys Asp Lys Gly Leu Gln Ser Leu Thr Leu Asp Gln Ser
545                 550                 555                 560

Val Arg Lys Asn Glu Lys Leu Lys Leu Ala Ala Gln Gly Ala Glu Lys
                    565                 570                 575

Thr Tyr Gly Asn Gly Asp Ser Leu Asn Thr Gly Lys Leu Lys Asn Asp
                580                 585                 590

Lys Val Ser Arg Phe Asp Phe Ile Arg Gln Ile Glu Val Asp Gly Gln
            595                 600                 605

Leu Ile Thr Leu Glu Ser Gly Glu Phe Gln Val Tyr Lys Gln Ser His
    610                 615                 620

Ser Ala Leu Thr Ala Phe Gln Thr Glu Gln Ile Gln Asp Ser Glu His
625                 630                 635                 640

Ser Gly Lys Met Val Ala Lys Arg Gln Phe Arg Ile Gly Asp Ile Ala
                    645                 650                 655

Gly Glu His Thr Ser Phe Asp Lys Leu Pro Glu Gly Gly Arg Ala Thr
                660                 665                 670

Tyr Arg Gly Thr Ala Phe Gly Ser Asp Asp Ala Gly Gly Lys Leu Thr
            675                 680                 685

Tyr Thr Ile Asp Phe Ala Ala Lys Gln Gly Asn Gly Lys Ile Glu His
    690                 695                 700

Leu Lys Ser Pro Glu Leu Asn Val Asp Leu Ala Ala Ala Asp Ile Lys
705                 710                 715                 720

Pro Asp Gly Lys Arg His Ala Val Ile Ser Gly Ser Val Leu Tyr Asn
                    725                 730                 735

Gln Ala Glu Lys Gly Ser Tyr Ser Leu Gly Ile Phe Gly Gly Lys Ala
                740                 745                 750

Gln Glu Val Ala Gly Ser Ala Glu Val Lys Thr Val Asn Gly Ile Arg
            755                 760                 765

His Ile Gly Leu Ala Ala Lys Gln
    770                 775
```

```
<210> SEQ ID NO 18
<211> LENGTH: 686
<212> TYPE: PRT
<213> ORGANISM: Neisseria meningitidis

<400> SEQUENCE: 18

Met Val Ser Ala Val Ile Gly Ser Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Arg Ala Arg Val Lys Ile Val Thr Tyr Gly Asn Val Thr Tyr
        130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
                260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Leu Gly Gly Glu His Thr Ala Phe
305                 310                 315                 320

Asn Gln Leu Pro Asp Gly Lys Ala Glu Tyr Arg Gly Thr Ala Phe Gly
                325                 330                 335

Ser Asp Asp Ala Gly Gly Lys Leu Thr Tyr Thr Ile Asp Phe Thr Lys
            340                 345                 350

Lys Gln Gly Asn Gly Lys Ile Glu His Leu Lys Ser Pro Glu Leu Asn
        355                 360                 365

Val Glu Leu Ala Ser Ala Glu Ile Lys Ala Asp Gly Lys Ser His Ala
    370                 375                 380
```

```
Val Ile Leu Gly Asp Val Arg Tyr Gly Ser Glu Lys Gly Ser Tyr
385                 390                 395                 400

Ser Leu Gly Ile Phe Gly Gly Arg Ala Gln Glu Val Ala Gly Ser Ala
            405                 410                 415

Glu Val Lys Thr Val Asn Gly Ile Arg His Ile Gly Leu Ala Ala Lys
            420                 425                 430

Gln Gly Ser Gly Gly Gly Val Ala Ala Asp Ile Gly Ala Gly Leu
        435                 440                 445

Ala Asp Ala Leu Thr Ala Pro Leu Asp His Lys Asp Lys Gly Leu Gln
450                 455                 460

Ser Leu Thr Leu Asp Gln Ser Val Arg Lys Asn Glu Lys Leu Lys Leu
465                 470                 475                 480

Ala Ala Gln Gly Ala Glu Lys Thr Tyr Gly Asn Gly Asp Ser Leu Asn
            485                 490                 495

Thr Gly Lys Leu Lys Asn Asp Lys Val Ser Arg Phe Asp Phe Ile Arg
            500                 505                 510

Gln Ile Glu Val Asp Gly Gln Leu Ile Thr Leu Glu Ser Gly Glu Phe
    515                 520                 525

Gln Val Tyr Lys Gln Ser His Ser Ala Leu Thr Ala Phe Gln Thr Glu
530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
            565                 570                 575

Pro Asp Gly Lys Ala Glu Tyr Arg Gly Thr Ala Phe Gly Ser Asp Asp
            580                 585                 590

Ala Gly Gly Lys Leu Thr Tyr Thr Ile Asp Phe Thr Lys Lys Gln Gly
            595                 600                 605

Asn Gly Lys Ile Glu His Leu Lys Ser Pro Glu Leu Asn Val Glu Leu
    610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Lys Gly Ser Tyr Ser Leu Gly
            645                 650                 655

Ile Phe Gly Gly Arg Ala Gln Glu Val Ala Gly Ser Ala Glu Val Lys
            660                 665                 670

Thr Val Asn Gly Ile Arg His Ile Gly Leu Ala Ala Lys Gln
            675                 680                 685
```

<210> SEQ ID NO 19
<211> LENGTH: 250
<212> TYPE: PRT
<213> ORGANISM: Neisseria meningitidis

<400> SEQUENCE: 19

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80
```

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Asp Val Arg Tyr Gly
        195                 200                 205

Gly Glu Glu Lys Gly Ser Tyr Ser Leu Gly Ile Phe Gly Gly Lys Ala
    210                 215                 220

Gln Glu Val Ala Gly Ser Ala Glu Val Lys Ile Arg Asn Gly Ile Arg
225                 230                 235                 240

His Ile Gly Leu Ala Ala Lys Gln Leu Glu
                245                 250

<210> SEQ ID NO 20
<211> LENGTH: 248
<212> TYPE: PRT
<213> ORGANISM: Neisseria meningitidis

<400> SEQUENCE: 20

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Thr Asp Lys Met Val Ala Lys Arg Gln Phe Arg Ile Ser Gly Ile Ala
        115                 120                 125

Gly Glu His Thr Ser Phe Asp Lys Leu Pro Glu Gly Gly Lys Ala Glu
    130                 135                 140

Tyr His Gly Lys Ala Phe Gly Ser Asp Asp Pro Asn Gly Arg Leu His
145                 150                 155                 160

Tyr Thr Ile Asp Phe Ala Ala Lys Gln Gly Asn Gly Arg Ile Glu His
                165                 170                 175

Leu Lys Ser Pro Glu Leu Asn Val Glu Leu Ala Ser Ala Asp Ile Lys
            180                 185                 190

Pro Asp Gly Lys Arg His Ala Val Ile Ser Gly Ser Val Leu Tyr Asn

```
                   195                 200                 205
Gln Ala Glu Lys Gly Ser Tyr Ser Leu Gly Ile Phe Gly Gly Lys Ala
    210                 215                 220
Gln Glu Val Ala Gly Ser Ala Glu Val Lys Thr Val Asn Gly Ile Arg
225                 230                 235                 240
His Ile Gly Leu Ala Ala Lys Gln
                245

<210> SEQ ID NO 21
<211> LENGTH: 248
<212> TYPE: PRT
<213> ORGANISM: Neisseria meningitidis

<400> SEQUENCE: 21

Val Ala Ala Asp Ile Gly Ala Gly Leu Ala Asp Ala Leu Thr Ala Pro
1               5                   10                  15
Leu Asp His Lys Asp Lys Gly Leu Gln Ser Leu Thr Leu Asp Gln Ser
                20                  25                  30
Val Arg Lys Asn Glu Lys Leu Lys Leu Ala Ala Gln Gly Ala Glu Lys
            35                  40                  45
Thr Tyr Gly Asn Gly Asp Ser Leu Asn Thr Gly Lys Leu Lys Asn Asp
        50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Val Tyr Lys Gln Ser His
                85                  90                  95
Ser Ala Leu Thr Ala Phe Gln Thr Glu Gln Ile Gln Asp Ser Glu His
                100                 105                 110
Ile Asp Lys Met Val Ala Lys Arg Gln Phe Arg Ile Ser Gly Ile Ala
            115                 120                 125
Gly Glu His Thr Ser Phe Asp Lys Leu Pro Glu Gly Gly Lys Ala Glu
        130                 135                 140
Tyr His Gly Lys Ala Phe Gly Ser Asp Asp Ala Gly Gly Lys Leu Thr
145                 150                 155                 160
Tyr Thr Ile Asp Phe Ala Ala Lys Gln Gly His Gly Arg Ile Glu His
                165                 170                 175
Leu Lys Ser Pro Glu Leu Asn Val Glu Leu Ala Ala Ala Asp Ile Lys
                180                 185                 190
Pro Asp Gly Lys Arg His Ala Val Ile Ser Gly Ser Val Leu Tyr Asn
            195                 200                 205
Gln Ala Glu Lys Gly Ser Tyr Ser Leu Gly Ile Phe Gly Gly Lys Ala
        210                 215                 220
Gln Glu Val Ala Gly Ser Ala Glu Val Lys Thr Val Asn Gly Ile Arg
225                 230                 235                 240
His Ile Gly Leu Ala Ala Lys Gln
                245

<210> SEQ ID NO 22
<211> LENGTH: 247
<212> TYPE: PRT
<213> ORGANISM: Neisseria meningitidis

<400> SEQUENCE: 22

Val Ala Ala Asp Ile Gly Ala Gly Leu Ala Asp Ala Leu Thr Ala Pro
1               5                   10                  15
Leu Asp His Lys Asp Lys Gly Leu Gln Ser Leu Thr Leu Asp Gln Ser
```

```
            20                  25                  30
Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Leu Gly
        115                 120                 125

Gly Glu His Thr Ala Phe Asn Gln Leu Pro Asp Gly Lys Ala Glu Tyr
    130                 135                 140

Arg Gly Thr Ala Phe Gly Ser Asp Asp Ala Gly Gly Lys Leu Thr Tyr
145                 150                 155                 160

Thr Ile Asp Phe Thr Lys Lys Gln Gly Asn Gly Lys Ile Glu His Leu
                165                 170                 175

Lys Ser Pro Glu Leu Asn Val Glu Leu Ala Ser Ala Glu Ile Lys Ala
            180                 185                 190

Asp Gly Lys Ser His Ala Val Ile Leu Gly Asp Val Arg Tyr Gly Ser
        195                 200                 205

Glu Glu Lys Gly Ser Tyr Ser Leu Gly Ile Phe Gly Gly Arg Ala Gln
    210                 215                 220

Glu Val Ala Gly Ser Ala Glu Val Lys Thr Val Asn Gly Ile Arg His
225                 230                 235                 240

Ile Gly Leu Ala Ala Lys Gln
                245

<210> SEQ ID NO 23
<211> LENGTH: 179
<212> TYPE: PRT
<213> ORGANISM: Neisseria meningitidis

<400> SEQUENCE: 23

Val Ser Ala Val Ile Gly Ser Ala Ala Val Gly Ala Lys Ser Ala Val
 1               5                  10                  15

Asp Arg Arg Thr Thr Gly Ala Gln Thr Asp Asp Asn Val Met Ala Leu
             20                  25                  30

Arg Ile Glu Thr Thr Ala Arg Ser Tyr Leu Arg Gln Asn Asn Gln Thr
         35                  40                  45

Lys Gly Tyr Thr Pro Gln Ile Ser Val Val Gly Tyr Asp Arg His Leu
     50                  55                  60

Leu Leu Leu Gly Gln Val Ala Thr Glu Gly Glu Lys Gln Phe Val Gly
 65                  70                  75                  80

Gln Ile Ala Arg Ser Glu Gln Ala Ala Glu Gly Val Tyr Asn Tyr Ile
                 85                  90                  95

Thr Val Ala Ser Leu Pro Arg Thr Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Arg Ala Arg Val Lys Ile Val Thr Tyr Gly Asn Val Thr Tyr Val
    130                 135                 140
```

```
Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 24
<211> LENGTH: 694
<212> TYPE: PRT
<213> ORGANISM: Neisseria meningitidis

<400> SEQUENCE: 24

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
50                  55                  60

Leu Leu Leu Leu Gly Gln Val Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
115                 120                 125

Ala Thr Arg Ala Arg Val Lys Ile Val Thr Tyr Gly Asn Val Thr Tyr
130                 135                 140

Val Met Gly Ile Leu Thr Pro Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
290                 295                 300

Lys Arg Gln Phe Arg Ile Gly Asp Leu Gly Gly Glu His Thr Ala Phe
305                 310                 315                 320

Asn Gln Leu Pro Asp Gly Lys Ala Glu Tyr Arg Gly Thr Ala Phe Gly
                325                 330                 335
```

```
Ser Asp Asp Ala Gly Gly Lys Leu Thr Tyr Thr Ile Asp Phe Thr Lys
                340                 345                 350

Lys Gln Gly Asn Gly Lys Ile Glu His Leu Lys Ser Pro Glu Leu Asn
            355                 360                 365

Val Glu Leu Ala Ser Ala Glu Ile Lys Ala Asp Gly Lys Ser His Ala
        370                 375                 380

Val Ile Leu Gly Asp Val Arg Tyr Gly Ser Glu Lys Gly Ser Tyr
385                 390                 395                 400

Ser Leu Gly Ile Phe Gly Gly Arg Ala Gln Glu Val Ala Gly Ser Ala
                405                 410                 415

Glu Val Lys Thr Val Asn Gly Ile Arg His Ile Gly Leu Ala Ala Lys
            420                 425                 430

Gln Gly Ser Gly Gly Gly Val Ala Ala Asp Ile Gly Ala Gly Leu
        435                 440                 445

Ala Asp Ala Leu Thr Ala Pro Leu Asp His Lys Asp Lys Gly Leu Gln
        450                 455                 460

Ser Leu Thr Leu Asp Gln Ser Val Arg Lys Asn Glu Lys Leu Lys Leu
465                 470                 475                 480

Ala Ala Gln Gly Ala Glu Lys Thr Tyr Gly Asn Gly Asp Ser Leu Asn
                485                 490                 495

Thr Gly Lys Leu Lys Asn Asp Lys Val Ser Arg Phe Asp Phe Ile Arg
            500                 505                 510

Gln Ile Glu Val Asp Gly Gln Leu Ile Thr Leu Glu Ser Gly Glu Phe
        515                 520                 525

Gln Val Tyr Lys Gln Ser His Ser Ala Leu Thr Ala Phe Gln Thr Glu
        530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
                565                 570                 575

Pro Asp Gly Lys Ala Glu Tyr Arg Gly Thr Ala Phe Gly Ser Asp Asp
            580                 585                 590

Ala Gly Gly Lys Leu Thr Tyr Thr Ile Asp Phe Thr Lys Lys Gln Gly
        595                 600                 605

Asn Gly Lys Ile Glu His Leu Lys Ser Pro Glu Leu Asn Val Glu Leu
        610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Lys Gly Ser Tyr Ser Leu Gly
                645                 650                 655

Ile Phe Gly Gly Arg Ala Gln Glu Val Ala Gly Ser Ala Glu Val Lys
            660                 665                 670

Thr Val Asn Gly Ile Arg His Ile Gly Leu Ala Ala Lys Gln Leu Glu
        675                 680                 685

His His His His His His
    690

<210> SEQ ID NO 25
<211> LENGTH: 687
<212> TYPE: PRT
<213> ORGANISM: Neisseria meningitidis

<400> SEQUENCE: 25

Met Val Ser Ala Val Ile Gly Ser Ala Ala Val Gly Ala Lys Ser Ala
1               5                   10                  15
```

```
Val Asp Arg Arg Thr Thr Gly Ala Gln Thr Asp Asn Val Met Ala
         20                  25                  30

Leu Arg Ile Glu Thr Thr Ala Arg Ser Tyr Leu Arg Gln Asn Asn Gln
 35                  40                  45

Thr Lys Gly Tyr Thr Pro Gln Ile Ser Val Val Gly Tyr Asp Arg His
 50                  55                  60

Leu Leu Leu Leu Gly Gln Val Ala Thr Glu Gly Lys Gln Phe Val
 65                  70                  75                  80

Gly Gln Ile Ala Arg Ser Glu Gln Ala Ala Glu Gly Val Tyr Asn Tyr
                 85                  90                  95

Ile Thr Val Ala Ser Leu Pro Arg Thr Ala Gly Asp Ile Ala Gly Asp
             100                 105                 110

Thr Trp Asn Thr Ser Lys Val Arg Ala Thr Leu Leu Gly Ile Ser Pro
             115                 120                 125

Ala Thr Arg Ala Arg Val Lys Ile Val Thr Tyr Gly Asn Val Thr Tyr
 130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                 165                 170                 175

Tyr Val Gln Arg Gly Ser Gly Gly Gly Val Ala Ala Asp Ile Gly
                 180                 185                 190

Ala Gly Leu Ala Asp Ala Leu Thr Ala Pro Leu Asp His Lys Asp Lys
         195                 200                 205

Gly Leu Gln Ser Leu Thr Leu Asp Gln Ser Val Arg Lys Asn Glu Lys
         210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                 245                 250                 255

Phe Ile Arg Gln Ile Glu Val Asp Gly Gln Leu Ile Thr Leu Glu Ser
             260                 265                 270

Gly Glu Phe Gln Val Tyr Lys Gln Ser His Ser Ala Leu Thr Ala Phe
             275                 280                 285

Gln Thr Glu Gln Ile Gln Asp Ser Glu His Ser Gly Lys Met Val Ala
 290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr His Gly Lys Ala Phe
                 325                 330                 335

Gly Ser Asp Asp Pro Asn Gly Arg Leu His Tyr Thr Ile Asp Phe Ala
             340                 345                 350

Ala Lys Gln Gly Tyr Gly Arg Ile Glu His Leu Lys Thr Pro Glu Gln
             355                 360                 365

Asn Val Asp Leu Ala Ala Ala Asp Ile Lys Pro Asp Gly Lys Arg His
 370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                 405                 410                 415

Ala Glu Val Lys Ile Gly Glu Gly Ile Arg His Ile Gly Leu Ala Ala
             420                 425                 430
```

```
Lys Gln Gly Ser Gly Gly Gly Val Ala Ala Asp Ile Gly Ala Gly
                435                 440                 445

Leu Ala Asp Ala Leu Thr Ala Pro Leu Asp His Lys Asp Lys Gly Leu
    450                 455                 460

Gln Ser Leu Thr Leu Asp Gln Ser Val Arg Lys Asn Glu Lys Leu Lys
465                 470                 475                 480

Leu Ala Ala Gln Gly Ala Glu Lys Thr Tyr Gly Asn Gly Asp Ser Leu
                485                 490                 495

Asn Thr Gly Lys Leu Lys Asn Asp Lys Val Ser Arg Phe Asp Phe Ile
                500                 505                 510

Arg Gln Ile Glu Val Asp Gly Gln Leu Ile Thr Leu Glu Ser Gly Glu
                515                 520                 525

Phe Gln Val Tyr Lys Gln Ser His Ser Ala Leu Thr Ala Phe Gln Thr
    530                 535                 540

Glu Gln Ile Gln Asp Ser Glu His Ser Gly Lys Met Val Ala Lys Arg
545                 550                 555                 560

Gln Phe Arg Ile Gly Asp Leu Gly Gly Glu His Thr Ala Phe Asn Gln
                565                 570                 575

Leu Pro Asp Gly Lys Ala Glu Tyr Arg Gly Thr Ala Phe Gly Ser Asp
                580                 585                 590

Asp Ala Gly Gly Lys Leu Thr Tyr Thr Ile Asp Phe Thr Lys Lys Gln
                595                 600                 605

Gly Asn Gly Lys Ile Glu His Leu Lys Ser Pro Glu Leu Asn Val Glu
                610                 615                 620

Leu Ala Ser Ala Glu Ile Lys Ala Asp Gly Lys Ser His Ala Val Ile
625                 630                 635                 640

Leu Gly Asp Val Arg Tyr Gly Ser Glu Glu Lys Gly Ser Tyr Ser Leu
                645                 650                 655

Gly Ile Phe Gly Gly Arg Ala Gln Glu Val Ala Gly Ser Ala Glu Val
                660                 665                 670

Lys Thr Val Asn Gly Ile Arg His Ile Gly Leu Ala Ala Lys Gln
                675                 680                 685

<210> SEQ ID NO 26
<211> LENGTH: 327
<212> TYPE: PRT
<213> ORGANISM: Neisseria meningitidis

<400> SEQUENCE: 26

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
                35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
                100                 105                 110

Leu Asp Ala Thr Thr Asn Ala Leu Asn Lys Leu Gly Glu Asn Ile Thr
                115                 120                 125
```

```
Thr Phe Ala Glu Glu Thr Lys Thr Asn Ile Val Lys Ile Asp Glu Lys
        130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
        210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
                260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
        290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```

ADJUVANT COMPRISING ALUMINUM, OLIGONUCLEOTIDE AND POLYCATION

This application claims the benefit of U.S. provisional application 61/237,595 filed Aug. 27, 2009, the complete contents of which are hereby incorporated herein by reference for all purposes.

"The content of the following submission on ASCII text file is incorporated herein by reference in its entirety: a computer readable form (CRF) of the Sequence Listing (file name: 53754_SeqListing.TXT, date recorded: Nov. 8, 2010, size: 100 KB)".

TECHNICAL FIELD

This invention is in the field of vaccine adjuvants and their combinations.

BACKGROUND ART

Adjuvants are included in many current vaccines. Aluminium salts, typically aluminium hydroxide or aluminium phosphate, are by far the most common adjuvants. Although they are usually used as single adjuvants, they have also been combined with other non-aluminium adjuvants e.g. the FENDRIX™ product includes an adjuvant of aluminium phosphate plus 3d-MPL, and the CERVARIX™ product's adjuvant is aluminium hydroxide plus 3d-MPL.

It is an object of the invention to provide modified and improved combination adjuvants which include aluminium salts.

DISCLOSURE OF THE INVENTION

The invention provides an immunological adjuvant comprising an aluminium salt, an immunostimulatory oligonucleotide and a polycationic polymer. The oligonucleotide and the polymer ideally associate with each other to form a complex.

The invention also provides an immunogenic composition comprising (i) an adjuvant of the invention and (ii) an immunogen. The immunogen can be: adsorbed to aluminium salt in the adjuvant; adsorbed to oligonucleotide/polymer complex in the adjuvant; and/or adsorbed to neither the aluminium salt nor complex.

The invention also provides a process for preparing an immunological adjuvant of the invention, comprising a step of mixing an aluminium salt with a complex of an immunostimulatory oligonucleotide and a polycationic polymer. In alternative methods, the aluminium salt, immunostimulatory oligonucleotide and polycationic polymer are mixed before the complex has formed. For example, the aluminium salt can be mixed with the oligonucleotide, and then the polymer is added; or the aluminium salt can be mixed with the polymer, and then the oligonucleotide is added. The complex may form after the oligonucleotide and the polymer meet.

The invention also provides a process for preparing an immunogenic composition comprising a step of mixing (i) an adjuvant of the invention and (ii) an immunogen.

The immunogen, aluminium salt, oligonucleotide and polymer may be mixed in any order. For example, the invention provides a process for preparing an immunogenic composition of the invention, comprising a step of mixing (i) an aluminium salt and (ii) an immunogen; and then mixing the salt/immunogen mixture with an immunostimulatory oligonucleotide and a polycationic polymer. The invention also provides a process for preparing an immunogenic composition of the invention, comprising a step of mixing (i) an immunostimulatory oligonucleotide and a polycationic polymer, typically in the form of a complex, and (ii) an immunogen; and then mixing the oligonucleotide/polymer/immunogen mixture with an aluminium salt. In one preferred embodiment, an immunogen is adsorbed to an aluminium salt (e.g. an aluminium hydroxide adjuvant) and the adsorbed immunogen is then mixed with oligonucleotide/cationic polymer complexes.

The invention also provides a kit comprising: (i) a first container that contains an adjuvant of the invention; and (ii) a second container that contains an immunogen and/or a further adjuvant. The invention also provides a kit comprising: (i) a first container that contains an aluminium salt; and (ii) a second container that contains an immunostimulatory oligonucleotide and a polycationic polymer. One or both of the first and second containers may include an immunogen. Thus the contents of the two containers can be combined (e.g. at the point of use) to form an adjuvant or immunogenic composition of the invention. These kits may include a third container that contains an immunogen and/or a further adjuvant.

The Aluminium Salt

Adjuvants of the invention include at least one aluminium salt. Suitable aluminium salts include the adjuvants known individually as aluminium hydroxide and aluminium phosphate. These names are conventional, but are used for convenience only, as neither is a precise description of the actual chemical compound which is present [e.g. see chapter 9 of reference 1]. The invention can use any of the "hydroxide" or "phosphate" adjuvants that are in general use as adjuvants. The use of an aluminium hydroxide adjuvant is preferred.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 1]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. Mean particle diameters in the range of 1-10 μm are reported in reference 2. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [chapter 9 of ref. 1]. The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants. The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

A mixture of both an aluminium hydroxide and an aluminium phosphate has can also be used. In this situation there may be more aluminium phosphate than hydroxide e.g. a weight ratio of at least 2:1 e.g. ≥5:1, ≥6:1, ≥7:1, ≥8:1, ≥9:1, etc.

Thus an adjuvant of the invention may comprise: (i) an aluminium hydroxide, an immunostimulatory oligonucleotide and a polycationic polymer; (ii) an aluminium phosphate, an immunostimulatory oligonucleotide and a polycationic polymer; or (iii) an aluminium hydroxide, an aluminium phosphate, an immunostimulatory oligonucleotide and a polycationic polymer.

The concentration of $Al^{+++}$ in a pharmaceutical composition of the invention will usually be <10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml.

The Immunostimulatory Oligonucleotide and the Polycationic Polymer

The invention uses an immunostimulatory oligonucleotide and a polycationic polymer. These are ideally associated with each other to form a particulate complex, which usefully is a TLR9 agonist.

Immunostimulatory oligonucleotides are known as useful adjuvants. They often contain a CpG motif (a dinucleotide sequence containing an unmethylated cytosine linked to a guanosine) and their adjuvant effect is discussed in refs. 3-8. Oligonucleotides containing TpG motifs, palindromic sequences, multiple consecutive thymidine nucleotides (e.g. TTTT), multiple consecutive cytosine nucleotides (e.g. CCCC) or poly(dG) sequences are also known immunostimulants, as are double-stranded RNAs. Although any of these various immunostimulatory oligonucleotides can be used with the invention, it is preferred to use an oligodeoxynucleotide containing deoxyinosine and/or deoxyuridine [9], and ideally an oligodeoxynucleotide containing deoxyinosine and deoxycytosine. Inosine-containing oligodeoxynucleotides may include a CpI motif (a dinucleotide sequence containing a cytosine linked to an inosine). The oligodeoxynucleotide may include more than one (e.g. 2, 3, 4, 5, 6 or more) CpI motif, and these may be directly repeated (e.g. comprising the sequence $(CI)_x$, where x is 2, 3, 4, 5, 6 or more) or separated from each other (e.g. comprising the sequence $(CIN)_x$, where x is 2, 3, 4, 5, 6 or more, and where each N independently represents one or more nucleotides). Cytosine residues are ideally unmethylated.

The oligonucleotides will typically have between 10 and 100 nucleotides e.g. 15-50 nucleotides, 20-30 nucleotides, or 25-28 nucleotides. It will typically be single-stranded.

The oligonucleotide can include exclusively natural nucleotides, exclusively non-natural nucleotides, or a mix of both. For instance, it may include one or more phosphorothioate linkage(s), and/or one or more nucleotides may have a 2'-O-methyl modification.

A preferred oligonucleotide for use with the invention is a single-stranded deoxynucleotide comprising the 26-mer sequence 5'-$(IC)_{13}$-3' (SEQ ID NO: 1). This oligodeoxynucleotide forms stable complexes with polycationic polymers to give a good adjuvant.

The polycationic polymer is ideally a polycationic peptide, such as a cationic antimicrobial peptide. The polymer may include one or more leucine amino acid residue(s) and/or one or more lysine amino acid residue(s). The polymer may include one or more arginine amino acid residue(s). It may include at least one direct repeat of one of these amino acids e.g. one or more Leu-Leu dipeptide sequence(s), one or more Lys-Lys dipeptide sequence(s), or one or more Arg-Arg dipeptide sequence(s). It may include at least one (and preferably multiple e.g. 2 or 3) Lys-Leu dipeptide sequence(s) and/or at least one (and preferably multiple e.g. 2 or 3) Lys-Leu-Lys tripeptide sequence(s).

The peptide may comprise a sequence $R_1$—$XZXZ_xXZX$—$R_2$, wherein: x is 3, 4, 5, 6 or 7; each X is independently a positively-charged natural and/or non-natural amino acid residue; each Z is independently an amino acid residue L, V, I, F or W; and $R_1$ and $R_2$ are independently selected from the group consisting of —H, —$NH_2$, —$COCH_3$, or —COH. In some embodiments X—$R_2$ may be an amide, ester or thioester of the peptide's C-terminal amino acid residue. See also reference 10.

A polycationic peptide will typically have between 5 and 50 amino acids e.g. 6-20 amino acids, 7-15 amino acids, or 9-12 amino acids.

A peptide can include exclusively natural amino acids, exclusively non-natural amino acids, or a mix of both. It may include L-amino acids and/or D-amino acids. L-amino acids are typical.

A peptide can have a natural N-terminus ($NH_2$—) or a modified N-terminus e.g. a hydroxyl, acetyl, etc. A peptide can have a natural C-terminus (—COOH) or a modified C-terminus e.g. a hydroxyl, an acetyl, etc. Such modifications can improve the peptide's stability.

A preferred peptide for use with the invention is the 11-mer KLKLLLLLKLK (SEQ ID NO: 2; ref. 11), with all L-amino acids. The N-terminus may be deaminated and the C-terminus may be hydroxylated. A preferred peptide is H—$KLKL_5KLK$—OH, with all L-amino acids. This oligopeptide is a known antimicrobial [12], neutrophil activator [13] and adjuvant [14] and forms stable complexes with immunostimulatory oligonucleotides to give a good adjuvant.

The most preferred mixture of immunostimulatory oligonucleotide and polycationic polymer is the TLR9 agonist known as IC31™ [15-17], which is an adsorptive complex of oligodeoxynucleotide SEQ ID NO: 1 and polycationic oligopeptide SEQ ID NO: 2.

The oligonucleotide and oligopeptide can be mixed together at various ratios, but they will generally be mixed with the peptide at a molar excess. The molar excess may be at least 5:1 e.g. 10:1, 15:1, 20:1, 25:1, 30;1, 35:1, 40:1 etc. A molar ratio of about 25:1 is ideal [18,19]. Mixing at this excess ratio can result in formation of insoluble particulate complexes between oligonucleotide and oligopeptide. The complexes can be combined with an aluminium salt as described herein.

The oligonucleotide and oligopeptide will typically be mixed under aqueous conditions e.g. a solution of the oligonucleotide can be mixed with a solution of the oligopeptide with a desired ratio. The two solutions may be prepared by dissolving dried (e.g. lyophilised) materials in water or buffer to form stock solutions that can then be mixed.

The complexes can be analysed using the methods disclosed in reference 20. Complexes with an average diameter in the range 1 μm-20 μm are typical.

Poly-arginine and CpG oligodeoxynucleotides similarly form complexes [21].

The complexes can be maintained in aqueous suspension e.g. in water or in buffer. Typical buffers for use with the complexes are phosphate buffers (e.g. phosphate-buffered saline), Tris buffers, Tris/sorbitol buffers, borate buffers, succinate buffers, citrate buffers, histidine buffers, etc. As an alternative, complexes may sometimes be lyophilised.

Complexes in aqueous suspension can be centrifuged to separate them from bulk medium (e.g. by aspiration, decanting, etc.). These complexes can then be re-suspended in an alternative medium if desired.

Mixing of Aluminium Salt, Oligonucleotide and Polymer

Adjuvant compositions of the invention can conveniently be prepared by mixing an aqueous suspension of the aluminium salt with an aqueous suspension of the oligonucleotide/polymer complex. The salt and complex are each typically maintained in liquid form, hence providing an easy way of co-formulating them.

In some embodiments one or both of the suspensions includes an immunogen so that the mixing provides an immunogenic composition of the invention. In other embodiments neither liquid includes an immunogen, so the mixed product (i.e. the adjuvant composition of the invention) can later be combined with an immunogen to provide an immunogenic composition of the invention.

Where two liquids are mixed the volume ratio for mixing can vary (e.g. between 20:1 and 1:20, between 10:1 and 1:10, between 5:1 and 1:5, between 2:1 and 1:2, etc.) but is ideally about 1:1. The concentration of components in the two suspensions can be selected so that a desired final concentration is achieved after mixing e.g. both may be prepared at 2× strength such that 1:1 mixing provides the final desired concentrations.

It is also possible to prepare the adjuvant composition in other ways e.g. by centrifuging the aluminium salt and then resuspending the pellet in a suspension of the complex, by centrifuging the complexes and then resuspending the pellet in a suspension of the aluminium salt, etc.

Various concentrations of oligonucleotide and polycationic polymer can be used e.g. any of the concentrations used in references 15, 18, 19 or 22. For example, a polycationic oligopeptide can be present at 1100 μM, 1000 μM, 350 μM, 220 μM, 200 μM, 110 μM, 100 μM, 11 μM, 10 μM, 1 μM, 500 nM, 50 nM, etc. An oligonucleotide can be present at 44 nM, 40 nM, 20 nM, 14 nM, 4.4 nM, 4 nM, 2 nM, etc. A polycationic oligopeptide concentration of less than 2000 nM is typical. For SEQ ID NOs: 1 & 2, mixed at a molar ratio of 1:25, the concentrations in mg/mL in three embodiments of the invention may thus be 0.311 & 1.322, or 0.109 & 0.463, or 0.031 and 0.132.

An aluminium salt and a complex of the immunostimulatory oligonucleotide and polycationic polymer are typically both particulate. The mean particle diameter of aluminium salt adjuvants is typically in the order of 1-20 μm [2,23]. This is also the size range for complexes seen in IC31™. When such particles are combined, the average diameter of the salt particles may be substantially the same as the average diameter of the complexes. In other embodiments, however, the average diameter of the salt particles may be smaller than the average size of the complexes. In other embodiments, the average diameter of the salt particles may be larger than the average size of the complexes. Where the average diameters differ, the larger diameter may be greater by a factor of at least 1.05× e.g. 1.1×, 1.2×, 1.3×, 1.4×, 1.5×, 2×, 2.5×, 3× or more. If either the salt or the complex has particles with a range of diameters, but the average diameters differ, the ranges may or may not overlap. Thus the largest salt particle may be smaller than the smallest complex particles, or the largest complex particles may be smaller than the smallest salt particles.

Because the particles are generally too large to be filter sterilised, sterility of an adjuvant composition of the invention will typically be achieved by preparing the aluminium salt and the complex under sterile conditions, and then mixing them under sterile conditions. For instance, the components of the complex could be filter sterilised, and then mixed under sterile conditions to form sterile complexes. These sterile complexes could then be mixed with an autoclaved (sterile) aluminium salt adjuvant to provide a sterile adjuvant composition. This sterile adjuvant can then be mixed with a sterile immunogen to give an immunogenic composition suitable for patient administration.

The density of aluminium salt particles is typically different from the density of a complex of immunostimulatory oligonucleotide and polycationic polymer, which means that the two particles might be separated based on density e.g. by sucrose gradient.

A composition comprising a mixture of an aluminium salt, an immunostimulatory oligonucleotide and a polycationic polymer can also usefully include (i) a buffer, such as a histidine buffer e.g. 10 mM histidine buffer and/or (ii) 5-15 mg/ml sodium chloride e.g. 9 mg/ml sodium chloride. A composition including a histidine buffer can usefully have a pH in the range of 6.0 and 7.4 e.g. between 6.3 and 7.0, or about 6.5.

Pharmaceutical Compositions

Adjuvant compositions of the invention usually include components in addition to the aluminium salt, oligonucleotide and polymer e.g. they typically include one or more pharmaceutically acceptable component. Such components may also be present in immunogenic compositions of the invention, originating either in the adjuvant composition or in another composition. A thorough discussion of such components is available in reference 24.

A composition may include a preservative such as thiomersal or 2-phenoxyethanol. It is preferred that the vaccine should be substantially free from (e.g. <10 μg/ml) mercurial material e.g. thiomersal-free. Vaccines containing no mercury are more preferred. Preservative-free vaccines are particularly preferred. α-tocopherol succinate can be included as an alternative to mercurial compounds in influenza vaccines.

To control tonicity, a composition may include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate, and/or magnesium chloride, etc.

Compositions may have an osmolality of between 200 mOsm/kg and 400 mOsm/kg, e.g. between 240-360 mOsm/kg, maybe within the range of 280-330 mOsm/mg or 290-310 mOsm/kg.

The pH of a composition will generally be between 5.0 and 8.1, and more typically between 6.0 and 8.0 e.g. 6.5 and 7.5, or between 7.0 and 7.8.

A composition is preferably sterile. A composition is preferably non-pyrogenic e.g. containing <1 EU (endotoxin unit, a standard measure) per dose, and preferably <0.1 EU per dose. A composition is preferably gluten free.

A useful composition comprises a histidine buffer (e.g. 10 mM histidine buffer), sodium chloride (e.g. 9 mg/ml sodium chloride) and an aluminium hydroxide adjuvant (e.g. 2 mg/ml Al$^{+++}$).

An immunogenic composition may include material for a single immunisation, or may include material for multiple immunisations (i.e. a 'multidose' kit). The inclusion of a preservative is useful in multidose arrangements. As an alternative (or in addition) to including a preservative in multidose compositions, the compositions may be contained in a container having an aseptic adaptor for removal of material.

Compositions will generally be in aqueous form at the point of administration. Vaccines are typically administered in a dosage volume of about 0.5 ml, although a half dose (i.e. about 0.25 ml) may sometimes be administered e.g. to children. In some embodiments of the invention a composition may be administered in a higher dose e.g. about 1 ml e.g. after mixing two 0.5 ml volumes.

Immunogens

Adjuvant compositions of the invention can be administered to animals in combination with immunogens to induce an immune response. The invention can be used with a wide range of immunogens, for treating or protecting against a wide range of diseases. The immunogen may elicit an immune response that protects against a viral disease (e.g. due to an enveloped or non-enveloped virus), a bacterial disease (e.g. due to a Gram negative or a Gram positive bacterium), a fungal disease, a parasitic disease, an auto-immune disease, or any other disease. The immunogen may also be useful in immunotherapy e.g. for treating a tumour/cancer, Alzheimer's disease, or an addiction.

The immunogen may take various forms e.g. a whole organism, an outer-membrane vesicle, a protein, a saccharide, a liposaccharide, a conjugate (e.g. of a carrier and a hapten, or of a carrier and a saccharide or liposaccharide), etc.

The immunogen may elicit an immune response against an influenza virus, including influenza A and B viruses. Various forms of influenza virus immunogen are currently available, typically based either on live virus or on inactivated virus. Inactivated vaccines may be based on whole virions, split virions, or on purified surface antigens. Influenza antigens can also be presented in the form of virosomes. Hemagglutinin is the main immunogen in current inactivated vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [25,26]). Thus compositions may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 3.75, about 1.9, about 1.5, etc. per strain. It is usual to include substantially the same mass of HA for each strain included in the vaccine e.g. such that the HA mass for each strain is within 10% of the mean HA mass per strain, and preferably within 5% of the mean. For live vaccines, dosing is measured by median tissue culture infectious dose (TCID$_{50}$) rather than HA content, and a TCID$_{50}$ of between $10^6$ and $10^8$ (preferably between $10^{6.5}$-$10^{7.5}$) per strain is typical. Rather than use SPF eggs as the substrate for viral growth, where virus is harvested from infected allantoic fluids of hens' eggs, cell lines that support influenza virus replication may be used. The cell line will typically be of mammalian origin e.g. MDCK. Influenza A virus immunogens may be from any suitable HA subtype strain e.g. H1, H3, H5, H7, H9 etc., such as a H1N1, H3N2 and/or H5N1 strain.

The immunogen may elicit an immune response against a *Candida* fungus such as *C. albicans*. For instance, the immunogen may be a β-glucan, which may be conjugated to a carrier protein. The glucan may include β-1,3 and/or β-1,6 linkages. Suitable immunogens include those disclosed in references 27 & 28.

The immunogen may elicit an immune response against a *Streptococcus* bacterium, including *S. agalactiae*, *S. pneumoniae* and *S. pyogenes*. For instance, the immunogen may be a capsular saccharide, which may be conjugated to a carrier protein. For *S. agalactiae* the saccharide may be from one or more of serotypes Ia, Ib, II, III, and/or V. For *S. pneumoniae* the saccharide may be from one or more of serotypes 1, 3, 4, 5, 6B, 7F, 9V, 14, 18C, 19F, and/or 23F. In addition to (or in place of) capsular saccharide immunogen(s), polypeptide immunogens may be used to elicit a protective anti-streptococcal immune response e.g. comprising RrgB, as disclosed in reference 29.

The immunogen may elicit an immune response against a *Staphylococcus* bacterium, including *S. aureus* or *S. epidermidis*. For instance, the immunogen may comprise an IsdA antigen, an IsdB antigen, a ClfA antigen, a ClfB antigen, a SdrD antigen, a Spa antigen, an EsxA antigen, an EsxB antigen, a Sta006 antigen, a hemolysin, and/or a Sta011 antigen. Suitable *S. aureus* immunogens and their combinations are disclosed in reference 30.

The immunogen may elicit an immune response against a meningococcal bacterium (*Neisseria meningitidis*). For instance, the immunogen may be a capsular saccharide, which may be conjugated to a carrier protein. Capsular saccharides are particularly useful for protecting against meningococcal serogroups A, C, W135 and/or Y. In addition to (or in place of) capsular saccharide immunogen(s), polypeptide immunogens and/or outer membrane vesicles may be used to elicit a protective anti-meningococcal immune response, particularly for use against serogroup B e.g. as disclosed in reference 31. Further details of useful serogroup B antigens are given below.

The immunogen may elicit an immune response against a hepatitis virus, such as a hepatitis A virus, a hepatitis B virus and/or a hepatitis C virus. For instance, the immunogen may be hepatitis B virus surface antigen (HBsAg). In some embodiments, though, the immunogen is not HBsAg (cf. ref. 32).

The immunogen may elicit an immune response against a respiratory syncytial virus. Immunogens may be from a group A RSV and/or a group B RSV. Suitable immunogens may comprise the F and/or G glycoproteins or fragments thereof e.g. as disclosed in references 33 & 34.

The immunogen may elicit an immune response against a *Chlamydia* bacterium, including *C. trachomatis* and *C. pneumoniae*. Suitable immunogens include those disclosed in references 35-41.

The immunogen may elicit an immune response against an *Escherichia coli* bacterium, including extraintestinal pathogenic strains. Suitable immunogens include those disclosed in references 42-45.

The immunogen may elicit an immune response against a coronavirus, such as the human SARS coronavirus. Suitable immunogens may comprise the spike glycoprotein.

The immunogen may elicit an immune response against a *Helicobacter pylori* bacterium. Suitable immunogens include CagA [46-49], VacA [50,51], and/or NAP [52-54].

The immunogen may elicit an immune response against rabies virus. A suitable immunogen is an inactivated rabies virus [55, RabAvert™].

The immunogen may elicit an immune response against a human papillomavirus. Useful immunogens are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [56]. In addition to HPV-16 and HPV-18 strains, it is also possible to include L1 VLPs from HPV-6 and HPV-11 strains.

The immunogen may elicit an immune response against a tumour antigen, such as MAGE-1, MAGE-2, MAGE-3 (MAGE-A3), MART-1/Melan A, tyrosinase, gp100, TRP-2, etc. The immunogen may elicit an immunotherapeutic response against lung cancer, melanoma, breast cancer, prostate cancer, etc.

The immunogen may elicit an immune response against a hapten conjugated to a carrier protein, where the hapten is a drug of abuse [57]. Examples include, but are not limited to, opiates, marijuana, amphetamines, cocaine, barbituates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

Various other immunogens may be used.

Serogroup B Meningococcus

Adjuvants of the invention are useful for enhancing an immune response against meningococcus, and in particular serogroup B meningococcus ("NmB"). Suitable immunogens for eliciting anti-NmB responses include polypeptide antigens, lipooligosaccharide and/or membrane vesicles.

Meningococcal Polypeptide Antigens

A composition may include one or more meningococcal polypeptide antigen(s). For instance, a composition may include a polypeptide antigen selected from the group consisting of: 287, NadA, NspA, HmbR, NhhA, App, Omp85, and/or fHBP. These antigens will usefully be present as purified polypeptides e.g. recombinant polypeptides. The antigen will preferably elicit bactericidal anti-meningococcal antibodies after administration to a subject.

A composition of the invention may include a 287 antigen. The 287 antigen was included in the published genome sequence for meningococcal serogroup B strain MC58 [58] as gene NMB2132 (GenBank accession number GI:7227388; SEQ ID NO: 3 herein). The sequences of 287 antigen from many strains have been published since then. For example, allelic forms of 287 can be seen in FIGS. 5 and 15 of reference 59, and in example 13 and FIG. 21 of reference 60 (SEQ IDs 3179 to 3184 therein). Various immunogenic fragments of the 287 antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 3. The most useful 287 antigens of the invention can elicit antibodies which, after administration to a subject, can bind to a meningococcal polypeptide consisting of amino acid sequence SEQ ID NO: 3. Advantageous 287 antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [58] as gene NMB1994 (GenBank accession number GI:7227256; SEQ ID NO: 4 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 4. The most useful NadA antigens of the invention can elicit antibodies which, after administration to a subject, can bind to a meningococcal polypeptide consisting of amino acid sequence SEQ ID NO: 4. Advantageous NadA antigens for use with the invention can elicit bactericidal anti-meningococcal antibodies after administration to a subject. SEQ ID NO: 6 is one such fragment.

A composition of the invention may include a NspA antigen. The NspA antigen was included in the published genome sequence for meningococcal serogroup B strain MC58 [58] as gene NMB0663 (GenBank accession number GI:7225888; SEQ ID NO: 5 herein). The antigen was previously known from references 61 & 62. The sequences of NspA antigen from many strains have been published since then. Various immunogenic fragments of NspA have also been reported. Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 5. The most useful NspA antigens of the invention can elicit antibodies which, after administration to a subject, can bind to a meningococcal polypeptide consisting of amino acid sequence SEQ ID NO: 5. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [58] as gene NMB1668 (SEQ ID NO: 12 herein). The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 12, where the value of i is 50, 60, 70, 80, 90, 95, 99 or more. In other embodiments a HmbR sequence used according to the invention may comprise a fragment of at least j consecutive amino acids from SEQ ID NO: 12, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 12 and/or (ii) comprising a fragment of at least j consecutive amino acids from SEQ ID NO: 12. Preferred fragments of j amino acids comprise an epitope from SEQ ID NO: 12. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 63. The most useful HmbR antigens of the invention can elicit antibodies which, after administration to a subject, can bind to a meningococcal polypeptide consisting of amino acid sequence SEQ ID NO: 12. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [58] as gene NMB0992 (GenBank accession number GI:7226232; SEQ ID NO: 6 herein). The sequences of NhhA antigen from many strains have been published since e.g. refs 59 & 64, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most useful NhhA antigens of the invention can elicit antibodies which, after administration to a subject, can bind to a meningococcal polypeptide consisting of amino acid sequence SEQ ID NO: 6. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [58] as gene NMB1985 (GenBank accession number GI:7227246; SEQ ID NO: 7 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 7. The most useful App antigens of the invention can elicit antibodies which, after administration to a subject, can bind to a meningococcal polypeptide consisting of amino acid sequence SEQ ID NO: 7. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [58] as gene NMB0182 (GenBank accession number GI:7225401; SEQ ID NO: 8 herein). The sequences of Omp85 antigen from many strains have been published since then. Further information on Omp85 can be found in references 65 and 66. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 8. The most useful Omp85 antigens of the invention can elicit antibodies which, after administration to a subject, can bind to a meningococcal polypeptide consisting of amino acid sequence SEQ ID NO: 8. Advantageous Omp85 antigens for use with the invention can elicit bactericidal anti-meningococcal antibodies after administration to a subject.

A composition of the invention may include at least one meningococcal factor H binding protein (fHBP). The fHBP antigen has been characterised in detail. It has also been called protein '741' [SEQ IDs 2535 & 2536 in ref. 60], 'NMB1870', 'GNA1870' [refs. 67-69], 'P2086', 'LP2086' or 'ORF2086' [70-72]. It is naturally a lipoprotein and is expressed across all meningococcal serogroups. The fHBP antigen falls into three distinct variants [73] and it has been found that serum raised against a given family is bactericidal within the same family, but is not active against strains which express one of the other two families i.e. there is intra-family cross-protection, but not inter-family cross-protection. Compositions of the invention can include a single fHBP variant, but advantageously include fHBP from two or three of the variants [73]. Advantageous fHBP antigens for use with the invention can elicit bactericidal anti-meningococcal antibodies after administration to a subject.

Where a composition comprises a single fHBP variant, it may include one of the following:

(a) a first polypeptide comprising a first amino acid sequence, where the first amino acid sequence comprises an amino acid sequence (i) having at least a % sequence identity to SEQ ID NO: 9 and/or (ii) consisting of a fragment of at least x contiguous amino acids from SEQ ID NO: 9;

(b) a second polypeptide, comprising a second amino acid sequence, where the second amino acid sequence comprises an amino acid sequence (i) having at least b % sequence identity to SEQ ID NO: 10 and/or (ii) consisting of a fragment of at least y contiguous amino acids from SEQ ID NO: 10;

(c) a third polypeptide, comprising a third amino acid sequence, where the third amino acid sequence comprises an amino acid sequence (i) having at least c % sequence identity to SEQ ID NO: 11 and/or (ii) consisting of a fragment of at least z contiguous amino acids from SEQ ID NO: 11.

Where a composition comprises two different meningococcal fHBP antigens, it may include a combination of: (i) a first and second polypeptide as defined above; (ii) a first and third polypeptide as defined above; or (iii) a second and third polypeptide as defined above. A combination of a first and third polypeptide is preferred. The first and second polypeptides may be part of a single polypeptide (a fusion protein) comprising the first and second amino acid sequences.

Where a composition comprises three different meningococcal fHBP antigens, it may include a combination of: a first and second and third polypeptide as defined above, and these may be part of a single polypeptide (a fusion protein) comprising the first and second and third amino acid sequences. Such triple-fHBP fusion proteins are disclosed in references 74 and 75 e.g. SEQ ID NO: 17 herein.

Where a composition comprises two different meningococcal fHBP antigens, although these may share some sequences in common, the first, second and third polypeptides have different fHBP amino acid sequences.

A polypeptide comprising the first amino acid sequence will, when administered to a subject, elicit an antibody response comprising antibodies that bind to the wild-type meningococcus protein having amino acid sequence SEQ ID NO: 9 (MC58). In some embodiments some or all of these antibodies do not bind to the wild-type meningococcus protein having amino acid sequence SEQ ID NO: 10 or to the wild-type meningococcus protein having amino acid sequence SEQ ID NO: 11.

A polypeptide comprising the second amino acid sequence will, when administered to a subject, elicit an antibody response comprising antibodies that bind to the wild-type meningococcus protein having amino acid sequence SEQ ID NO: 10 (2996). In some embodiments some or all of these antibodies do not bind to the wild-type meningococcus protein having amino acid sequence SEQ ID NO: 9 or to the wild-type meningococcus protein having amino acid sequence SEQ ID NO: 11.

A polypeptide comprising the third amino acid sequence will, when administered to a subject, elicit an antibody response comprising antibodies that bind to the wild-type meningococcus protein having amino acid sequence SEQ ID NO: 11 (M1239). In some embodiments some or all of these antibodies do not bind to the wild-type meningococcus protein having amino acid sequence SEQ ID NO: 9 or to the wild-type meningococcus protein having amino acid sequence SEQ ID NO: 10.

In some embodiments the fragment of at least x contiguous amino acids from SEQ ID NO: 9 is not also present within SEQ ID NO: 10 or within SEQ ID NO: 11. Similarly, the fragment of at least y contiguous amino acids from SEQ ID NO: 10 might not also be present within SEQ ID NO: 9 or within SEQ ID NO: 11. Similarly, the fragment of at least z contiguous amino acids from SEQ ID NO: 11 might not also be present within SEQ ID NO: 9 or within SEQ ID NO: 10. In some embodiments, when said fragment from one of SEQ ID NOs: 9 to 11 is aligned as a contiguous sequence against the other two SEQ ID NOs, the identity between the fragment and each of the other two SEQ ID NOs is less than 75% e.g. less than 70%, less than 65%, less than 60%, etc.

The value of a is at least 80 e.g. 82, 84, 86, 88, 90, 92, 94, 95, 96, 97, 98, 99 or more. The value of b is at least 80 e.g. 82, 84, 86, 88, 90, 92, 94, 95, 96, 97, 98, 99 or more. The value of c is at least 80 e.g. 82, 84, 86, 88, 90, 92, 94, 95, 96, 97, 98, 99 or more. The values of a, b and c may be the same or different. In some embodiments, a b and c are identical.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z may be the same or different. In some embodiments, x y and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof.

In some embodiments fHBP polypeptide(s) are lipidated e.g. at a N-terminus cysteine. For lipidated fHBPs, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-glyceryl cysteine), etc.

A composition may include more than one meningococcal polypeptide antigen. For example, the composition may include three polypeptides: one comprising SEQ ID NO: 13, one comprising SEQ ID NO: 14, and a third comprising SEQ ID NO: 15 or 26 (see references 31 & 76). This combination of three polypeptides, covering five antigens, is particularly advantageous for protecting against serogroup B meningococcus. An alternative composition may include: a first polypeptide comprising SEQ ID NO: 13, a second polypeptide comprising SEQ ID NO: 15, and a third comprising SEQ ID NO: 17. An alternative composition may include: a first polypeptide comprising SEQ ID NO: 13, a second polypeptide comprising SEQ ID NO: 15, and a third comprising SEQ ID NO: 18. An alternative composition may include: a first polypeptide comprising SEQ ID NO: 13, a second polypeptide comprising SEQ ID NO: 26, and a third comprising SEQ ID NO: 17. An alternative composition may include: a first polypeptide comprising SEQ ID NO: 13, a second polypeptide comprising SEQ ID NO: 26, and a third comprising SEQ ID NO: 18.

Meningococcal Lipooligosaccharide

A composition may include one or more meningococcal lipooligosaccharide (LOS) antigen(s). Meningococcal LOS is a glucosamine-based phospholipid that is found in the outer monolayer of the outer membrane of the bacterium. It includes a lipid A portion and a core oligosaccharide region, with the lipid A portion acting as a hydrophobic anchor in the membrane. Heterogeneity within the oligosaccharide core generates structural and antigenic diversity among different meningococcal strains, which has been used to subdivide the strains into 12 immunotypes (L1 to L12). The invention may use LOS from any immunotype e.g. from L1, L2, L3, L4, L5, L6, L7 and/or L8.

The L2 and L3 α-chains naturally include lacto-N-neotetraose (LNnT). Where the invention uses LOS from a L2 or L3 immunotype this LNnT may be absent. This absence can be achieved conveniently by using mutant strains that are engineered to disrupt their ability to synthesise the LNnT tetrasaccharide within the α-chain. It is known to achieve this goal by knockout of the enzymes that are responsible for the relevant biosynthetic additions [77,107]. For instance, knockout of the LgtB enzyme prevents addition of the terminal galactose of LNnT, as well as preventing downstream addition of the α-chain's terminal sialic acid. Knockout of the LgtA enzyme prevents addition of the N-acetyl-glucosamine of LNnT, and also the downstream additions. LgtA knockout may be accompanied by LgtC knockout. Similarly, knockout of the LgtE and/or GalE enzyme prevents addition of internal galactose, and knockout of LgtF prevents addition of glucose to the Hep$^I$ residue. Any of these knockouts can be used, singly or in combination, to disrupt the LNnT tetrasaccharide in a L2, L3, L4, L7 or L9 immunotype strain. Knockout of at least LgtB is preferred, as this provides a LOS that retains useful immunogenicity while removing the LNnT epitope.

In addition to, or in place of, mutations to disrupt the LNnT epitope, a knockout of the galE gene also provides a useful modified LOS, and a lipid A fatty transferase gene may similarly be knocked out [78]. At least one primary O-linked fatty acid may be removed from LOS [79]. LOS having a reduced number of secondary acyl chains per LOS molecule can also be used [80]. The LOS will typically include at least the GlcNAc-$Hep_2$phosphoethanolamine-$KDO_2$-Lipid A structure [81]. The LOS may include a GlcNAcβ1-3Galβ1-4Glc trisaccharide while lacking the LNnT tetrasaccharide.

LOS may be included in various forms. It may be used in purified form on its own. It may be conjugated to a carrier protein. When LOS is conjugated, conjugation may be via a lipid A portion in the LOS or by any other suitable moiety e.g. its KDO residues. If the lipid A moiety of LOS is absent then such alternative linking is required. Conjugation techniques for LOS are known from e.g. references 79, 81, 82, 83, etc. Useful carrier proteins for these conjugates include e.g. bacterial toxins, such as diphtheria or tetanus toxins, or toxoids or mutants thereof.

The LOS may be from a strain (e.g. a genetically-engineered meningococcal strain) which has a fixed (i.e. not phase variable) LOS immunotype as described in reference 84. For example, L2 and L3 LOS immunotypes may be fixed. Such strains may have a rate of switching between immunotypes that is reduced by more than 2-fold (even >50_fold) relative to the original wild-type strain. Reference 84 discloses how this result can be achieved by modification of the lgtA and/or lgtG gene products.

LOS may be O-acetylated on a GlcNac residue attached to its Heptose II residue e.g. for L3 [85].

An immunogenic composition can include more than one type of LOS e.g. LOS from meningococcal immunotypes L2 and L3. For example, the LOS combinations disclosed in reference 86 may be used.

A LOS antigen can preferably elicit bactericidal anti-meningococcal antibodies after administration to a subject.

Membrane Vesicles

A composition may include meningococcal outer membrane vesicles. These include any proteoliposomic vesicle obtained by disruption of or blebbling from a meningococcal outer membrane to form vesicles therefrom that include protein components of the outer membrane. Thus the term includes OMVs (sometimes referred to as 'blebs'), microvesicles (MVs [87]) and 'native OMVs' ('NOMVs' [88]).

MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 89 & 90 describe *Neisseria* with high MV production.

OMVs are prepared artificially from bacteria, and may be prepared using detergent treatment (e.g. with deoxycholate), or by non-detergent means (e.g. see reference 91). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [92 & 93] being preferred for treating *Neisseria*) at a pH sufficiently high not to precipitate the detergent [94]. Other techniques may be performed substantially in the absence of detergent [91] using techniques such as sonication, homogenisation, microfluidisation, cavitation, osmotic shock, grinding, French press, blending, etc. Methods using no or low detergent can retain useful antigens such as NspA [91]. Thus a method may use an OMV extraction buffer with about 0.5% deoxycholate or lower e.g. about 0.2%, about 0.1%, <0.05% or zero.

A useful process for OMV preparation is described in reference 95 and involves ultrafiltration on crude OMVs, rather than instead of high speed centrifugation. The process may involve a step of ultracentrifugation after the ultrafiltration takes place.

Vesicles for use with the invention can be prepared from any meningococcal strain. The vesicles will usually be from a serogroup B strain, but it is possible to prepare them from serogroups other than B (e.g. reference 94 discloses a process for serogroup A), such as A, C, W135 or Y. The strain may be of any serotype (e.g. 1, 2a, 2b, 4, 14, 15, 16, etc.), any serosubtype, and any immunotype (e.g. L1; L2; L3; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 96] e.g. the ET-37 complex is the ST-11 complex by MLST, the ET-5 complex is ST-32 (ET-5), lineage 3 is ST-41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles used with the invention may be prepared from wild-type meningococcal strains or from mutant meningococcal strains. For instance, reference 97 discloses preparations of vesicles obtained from *N. meningitidis* with a modified fur gene. Reference 105 teaches that nspA expression should be up-regulated with concomitant porA and cps knockout. Further knockout mutants of *N. meningitidis* for OMV production are disclosed in references 105 to 107. Reference 98 discloses vesicles in which fHBP is upregulated. Reference 99 discloses the construction of vesicles from strains modified to express six different PorA subtypes. Mutant *Neisseria* with low endotoxin levels, achieved by knockout of enzymes involved in LPS biosynthesis, may also be used [100,101]. These or others mutants can all be used with the invention.

Thus a strain used with the invention may in some embodiments express more than one PorA subtype. 6-valent and 9-valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12-1,13; P1.7-2,4; P1.22,14; P1.7-1,1 and/or P1.18-1,3,6. In other embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76, as disclosed in reference 108).

In some embodiments a strain may hyper-express (relative to the corresponding wild-type strain) certain proteins. For instance, strains may hyper-express NspA, protein 287 [102], fHBP [98], TbpA and/or TbpB [103], Cu,Zn-superoxide dismutase [103], HmbR, etc.

In some embodiments a strain may include one or more of the knockout and/or hyper-expression mutations disclosed in references 104 to 107. Preferred genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [104]; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB [105]; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB [106]; and (d) CtrA, CtrB, CtrD, FrpB, OpA, OpC, PilC, PorB, SiaD, SynA, SynB, and/or SynC [107].

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no α chain.

If LOS is present in a vesicle it is possible to treat the vesicle so as to link its LOS and protein components ("intra-bleb" conjugation [107]).

The invention may be used with mixtures of vesicles from different strains. For instance, reference 108 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. Reference 109 also discloses useful combinations of different vesicles. A combination of vesicles from strains in each of the L2 and L3 immunotypes may be used in some embodiments.

Adsorption

Aluminium salt adjuvants are adsorptive i.e. immunogens can adsorb to the salts, by a variety of mechanisms. In some circumstances, however, immunogen and aluminium salt adjuvants can both be present in a composition without adsorption, either through an intrinsic property of the immunogen or because of steps taken during formulation (e.g. the use of an appropriate pH during formulation to prevent adsorption from occurring).

Preferred complexes of immunostimulatory oligonucleotide and polycationic polymer are also adsorptive.

In a mixture of aluminium salts and complexes, therefore, there can be multiple adsorptive opportunities for an immunogen: an immunogen can adsorb to aluminium salt, to a oligonucleotide/polymer complex, to both (in various proportions), or to neither. The invention covers all such arrangements. For example, in one embodiment an immunogen can be adsorbed to an aluminium salt, and the adsorbed immunogen/salt can then be mixed with an oligonucleotide/polymer complex. In another embodiment an immunogen can be adsorbed to an oligonucleotide/polymer complex, and the adsorbed immunogen/complex can then be mixed with an. aluminium salt. In another embodiment two immunogens (the same or different) can be separately adsorbed to an oligonucleotide/polymer complex and to an aluminium salt, and the two adsorbed components can then be mixed.

In some situations, an immunogen may change its adsorption status e.g. by a change in pH or temperature, or after mixing of components. Desorption of antigens from aluminium salts in vitro [110] and in vivo [111] is known. Desorption from one adsorptive particle followed by resorption to a different adsorptive particle can occur, thereby resulting in e.g. transfer of an immunogen from an aluminium salt adjuvant to a complex or vice versa. In some embodiments, a single antigen molecule or complex might adsorb to both an aluminium salt and a complex, forming a bridge between the two adsorptive particles.

If an immunogen adsorbs to an adsorptive component, it is not necessary for all of the immunogen to adsorb. This situation can occur because of an immunogen's intrinsic equilibrium between adsorbed and soluble phases, or because adsorptive surfaces are saturated. Thus the immunogen in a composition may be fully or partially adsorbed, and the adsorbed fraction can be on one or more different adsorptive components (e.g. on aluminium salt and/or on a oligonucleotide/polymer complex). In this situation, the adsorbed fraction may be at least 10% (by weight) of the total amount of that immunogen in the composition e.g. >20%, >30%, >40%, >50%, >60%, >70%, >80%, >90%, >95%, >98% or more. In some embodiments an immunogen is totally adsorbed i.e. none is detectable in the supernatant after centrifugation to separate complexes from bulk liquid medium. In other embodiments, though, none of a particular immunogen may be adsorbed.

In some circumstances it is possible that the immunostimulatory oligonucleotide and/or polycationic polymer component of a complex could adsorb to the aluminium salt. Preferably, though, the complexes remain intact after mixing with the aluminium salt. Also, to avoid adsorption of complexes to the aluminium salt (and vice versa) it is useful that the aluminium salt and the complexes have similar points of zero charge (isoelectric points) e.g. within 1 pH unit of each other. Thus useful complexes have a PZC of between 10 and 12, which is useful for combining with an aluminium hydroxide adjuvant having a PZC of about 11.

Packaging of Compositions or Kit Components

Suitable containers for adjuvant compositions, immunogenic compositions and kit components of the invention include vials, syringes (e.g. disposable syringes), etc. These containers should be sterile. The containers can be packaged together to form a kit e.g. in the same box.

Where a component is located in a vial, the vial can be made of a glass or plastic material. The vial is preferably sterilized before the composition is added to it. To avoid problems with latex-sensitive subjects, vials are preferably sealed with a latex-free stopper, and the absence of latex in all packaging material is preferred. The vial may include a single dose of vaccine, or it may include more than one dose (a 'multidose' vial) e.g. 10 doses. Useful vials are made of colorless glass. Borosilicate glasses are preferred to soda lime glasses. Vials may have stoppers made of butyl rubber.

A vial can have a cap (e.g. a Luer lock) adapted such that a syringe can be inserted into the cap. A vial cap may be located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. The plunger in a syringe may have a stopper to prevent the plunger from being accidentally removed during aspiration. The syringe may have a latex rubber cap and/or plunger. Disposable syringes contain a single dose of vaccine. The syringe will generally have a tip cap to seal the tip prior to attachment of a needle, and the tip cap may be made of a butyl rubber. If the syringe and needle are packaged separately then the needle is preferably fitted with a butyl rubber shield. Useful syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

It is usual in multi-component products to include more material than is needed for subject administration, so that a full final dose volume is obtained despite any inefficiency in material transfer. Thus an individual container may include overfill e.g. of 5-20% by volume.

Methods of Treatment, and Administration of Immunogenic Compositions

Compositions of the invention are suitable for administration to human subjects, and the invention provides a method of raising an immune response in a subject, comprising the step of administering an immunogenic composition of the invention to the subject.

The invention also provides a method of raising an immune response in a subject, comprising the step of mixing the contents of the containers of a kit of the invention and administering the mixed contents to the subject.

The invention also provides composition or kit of the invention for use as a medicament e.g. for use in raising an immune response in a subject.

The invention also provides the use of an aluminium salt, an immunostimulatory oligonucleotide and a polycationic polymer, in the manufacture of a medicament for raising an immune response in a subject. This medicament may be administered in combination with an immunogen.

The invention also provides the use of an aluminium salt, an immunostimulatory oligonucleotide, a polycationic polymer and an immunogen, in the manufacture of a medicament for raising an immune response in a subject.

These methods and uses will generally be used to generate an antibody response, preferably a protective antibody response.

Compositions of the invention can be administered in various ways. The usual immunisation route is by intramuscular injection (e.g. into the arm or leg), but other available routes include subcutaneous injection, intranasal, oral, buccal, sublingual, intradermal, transcutaneous, transdermal, etc.

Immunogenic compositions prepared according to the invention may be used as vaccines to treat both children and adults. A subject may be less than 1 year old, 1-5 years old, 5-15 years old, 15-55 years old, or at least 55 years old. Subjects for receiving the vaccines may be elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, people travelling abroad, etc. Aluminium salt adjuvants are routinely used in infant populations, and IC31™ has also been effective in this age group [22,112]. The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve subjects. Multiple doses will typically be administered at least 1 week apart (e.g. about 2 weeks, about 3 weeks, about 4 weeks, about 6 weeks, about 8 weeks, about 12 weeks, about 16 weeks, etc.).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, or for viral growth, it is preferably one that has been approved for use in human vaccine production e.g. as in Ph Eur general chapter 5.2.3.

In some embodiments, the invention does not encompass or use compositions which include an immunogen comprising amino acid sequence SEQ ID NO: 16 [113]. In embodiments where an immunogen comprising amino acid sequence SEQ ID NO: 16 is present in a composition, the aluminium salt will typically be aluminium hydroxide and/or the composition may include at least one further and different meningococcal immunogen.

MODES FOR CARRYING OUT THE INVENTION

Adjuvants

An aluminium hydroxide adjuvant suspension is prepared by standard methods. IC31 complexes were prepared as disclosed in reference 19. Adjuvant combinations were made my mixing the aluminium hydroxide adjuvant with IC31 complexes. The individual adjuvants (Al—H, IC31) and their mixture (Al—H+IC31) have been combined with antigens from various pathogens and tested in various animal models. Various orders of mixing Al—H, IC31 and antigen have been used.

Antigens tested so far are from pathogens including *N. meningitidis* serogroups A/B/C/W135/Y, extraintestinal pathogenic *E. coli, Streptococcus pyogenes, Candida albicans*, respiratory syncytial virus and *S. aureus*. These studies have mainly used polypeptide antigens, but also used saccharide antigens (meningococcal serogroups A, C, W135 & Y, and C. albicans).

Meningococcus (i)

The three polypeptides which make up the '5CVMB' vaccine disclosed in reference 31 were adjuvanted with aluminium hydroxide and/or IC31. The encoded polypeptides have amino acid sequences SEQ ID NO: 13, SEQ ID NO: 14 and SEQ ID NO: 15 (see refs. 31 & 76).

In a first set of experiments, nine groups of mice received 10 μg of antigens, 3 mg/ml of aluminium hydroxide and varying doses of IC31. Groups received the following nine compositions, with groups 7-9 receiving the same antigens as 1-6 but differently formulated:

|   | Antigen dose (μg) | IC31 volume* (μl) | Al—H (mg/ml) |
|---|---|---|---|
| 1 | 10 | 100 | 3 |
| 2 | 10 | 50 | 3 |
| 3 | 10 | 25 | 3 |
| 4 | 10 | 10 | 3 |
| 5 | 10 | 0 | 3 |
| 6 | 10 | 100 | 0 |
| 7 | 10 | 0 | 3 |
| 8 | 10 | 100 | 3 |
| 9 | 10 | 100 | 0 |

*A standard IC31 suspension was used. 100 μl of this suspension gave full-strength. Lower volumes gave lower strengths. To preserve the volume for the lower-strength compositions, buffer was added up to 100 μl.

Sera from the mice were tested against a panel of meningococcal strains for bactericidal activity. Bactericidal titers from experiment MP03 were as follows against six different strains, A to F:

|   | A | B | C | D | E | F |
|---|---|---|---|---|---|---|
| 1 | >65536 | 4096 | 8192 | 4096 | 256 | 32768 |
| 2 | >65536 | 8192 | 8192 | 8192 | 512 | >65536 |
| 3 | >65536 | 4096 | 4096 | 8192 | 512 | 32768 |
| 4 | >65536 | 2048 | 4096 | 4096 | 512 | 8192 |
| 5 | >65536 | 2048 | 4096 | 8192 | 256 | 32768 |
| 6 | >65536 | 4096 | >8192 | 8192 | 1024 | >65536 |
| 7 | >65536 | 2048 | 4096 | 4096 | 256 | 4096 |
| 8 | >65536 | >8192 | >8192 | >8192 | 512 | >65536 |
| 9 | 32768 | 8192 | >8192 | >8192 | 4096 | >65536 |

Thus the titers obtained with Al—H as the only adjuvant (group 5) were generally improved across the panel by the addition of IC31 at various ratios (groups 1 to 4). The same effect was seen with the different antigen formulation (compare groups 7 and 8)

Further studies on a wider panel confirmed that addition of IC31 improved the titers when compared to the use of Al—H alone. For instance, bactericidal titers using sera from groups 1, 3 and 5 against a panel of 16 strains (including A to F from above) were as follows, with 50% of strains in group 5 having a titer≥1:1024 but 56.25% in groups 1 and 3:

|   | 1 Al—H + IC31(100) | 3 Al—H + IC31(25) | 5 Al—H |
|---|---|---|---|
| A | >65536 | >65536 | >65536 |
| B | 4096 | 4096 | 2048 |
| C | 8192 | 4096 | 4096 |
| D | 4096 | 8192 | 8192 |
| E | 256 | 512 | 256 |
| F | 32768 | 32768 | 32768 |
| G | 4096 | 2048 | 2048 |
| H | 2048 | 2048 | 1024 |
| I | 64 | 256 | 64 |
| J | 512 | 256 | 128 |
| K | 256 | 256 | 256 |
| L | 512 | 512 | 512 |
| M | 2048 | 512 | 1024 |
| N | 1024 | 2048 | 512 |
| O | 128 | 64 | 64 |
| P | 512 | 1024 | 512 |

The nine compositions were tested for pH and osmolality. For compositions 1-5, 7 and 8 the pH was in the range of 6.2 to 6.6; compositions 6 and 9 had a slightly higher pH, in the range 6.9 to 7.3. Osmolality of all compositions was in the range of 280-330 mOsm/kg.

SDS-PAGE analysis of the supernatants of the compositions, and of compositions treated to desorb antigens, showed that the antigens adsorbed similarly to the mixture of Al—H+ IC31 as to Al—H alone: for all compositions containing Al—H, between 94-100% of each antigen was adsorbed.

Meningococcus (ii)

A triple-fusion polypeptide containing three variants of fHBP, in the order II-III-I (as disclosed in reference 17; SEQ ID NO: 17 herein), was adjuvanted with aluminium hydroxide and/or IC31.

In a first set of experiments, six groups of mice received 20 μg of antigen (with or without a purification tag), 3 mg/ml of aluminium hydroxide and 100 μl of IC31. Groups received the following:

|   | Antigen dose (μg) | Antigen tag | IC31 volume (μl) | Al—H (mg/ml) |
|---|---|---|---|---|
| 1 | 20 | No | 100 | 0 |
| 2 | 20 | Yes | 100 | 0 |
| 3 | 20 | No | 100 | 3 |
| 4 | 20 | Yes | 100 | 3 |
| 5 | 20 | No | 0 | 3 |
| 6 | 20 | Yes | 0 | 3 |

Sera from the mice were tested against a panel of meningococcal strains for bactericidal activity.

Bactericidal titers from experiment MP05 were again tested against a panel of strains (25 in total). 64% of strains in group 5 (Al—H, no tag) had a titer≥1:128, and 36% had a titer≥1:1024, but addition of IC31 (group 3) increased these figures to 76% and 56%, respectively. Similarly, 76% of strains in group 6 (Al—H, tag) had a titer≥1:128, and 64% had a titer≥1:1024, but addition of IC31 (group 4) increased these figures to 80% and 68%, respectively. For 23/25 strains the titers were the same or better in group 3 than in group 5; for 22/25 strains the titers were the same or better in group 4 than in group 6. Particularly good improvements were seen against strains NM008 and M4287, where very low titers of ≤1:32 were improved to between 1:256 and 1:4096.

The tag-free compositions (1, 3 and 5) were tested for pH and osmolality. The pH was in the range of 6.87 to 7.00. Osmolality was in the range of 302-308 mOsm/kg.

SDS-PAGE analysis of the supernatants of the tag-free compositions (1, 3 & 5), and of compositions treated to desorb the antigen, showed that the antigen adsorbed similarly to the mixture of Al—H+IC31 as to Al—H alone.

Further immunogenicity experiments used the $fHBP_{II-III-I}$ antigen in combination with the NadA and 287-953 antigens (SEQ ID NOs: 13 and 15) in experiment MP04, with the same groupings and strain panel. Titers in group 4 were the same or better than in group 6 for 24/25 strains; titers were the same or better in group 3 than in group 5 also for 24/25 strains. The proportion of strains where the sera had a bactericidal titer of at least 1:128 was 100% in each of groups 1 to 4 and in group 6, but only 84% in group 5. With a more stringent threshold of ≥1:1024, however, sera from groups 1 to 4 were bactericidal against 88% of strains, whereas the proportion was only 80% in group 6 and 56% in group 5. Thus the anti-meningococcus immune responses obtained with Al—H as the only adjuvant were generally improved across the panel by the addition of IC31.

Meningococcus (iii)

Reference 113 discloses various modified forms of fHBP, including:
PATCH_2S (SEQ ID NO: 19 herein)
PATCH_5bis (SEQ ID NO: 20 herein)
PATCH_5penta (SEQ ID NO: 21 herein)
PATCH_9C (SEQ ID NO: 16 herein)
PATCH_10A (SEQ ID NO: 22 herein)

These five modified fHBP proteins, and also PATCH_9F and the wild-type sequence from strain 2996, were used to immunise mice with aluminium hydroxide (Al—H), Al—H+ IC31, or IC31 alone. Sera were tested against a panel of ten different meningococcal strains. The titers against all 10 strains were as good as or higher in the Al—H+IC31 group than in both the Al—H group and the IC31 group for the PATCH_5B and PATCH_9C sequences.

More generally, the invention can be used with a protein comprising any one of SEQ ID NOs: 1 to 80 from reference 113.

The combination of Al—H+IC31 also gave better results than Al—H alone when tested with fusion proteins containing PATCH_9C and/or PATCH_10A and/or the wild-type MC58 fHBP sequence (comprising SEQ ID NO: 3) and/or 936 antigen (comprising SEQ ID NO: 23) e.g. converting efficacy against only 1/10 strains with Al—H into efficacy against 9/10 strains when using a fusion protein containing 936 fused to two copies of PATCH_10A (SEQ ID NO: 18).

Using the 936-10A-10A sequence or a 936-9C-10A sequence (SEQ ID NO: 25), bactericidal titers against a panel of 10 strains were:

|   | 936-10A-10A | | 936-9C-10A | |
|---|---|---|---|---|
|   | Al—H | Al—H + IC31 | Al—H | Al—H + IC31 |
| A | 8192 | ≥32768 | 8192 | ≥32768 |
| B | <16 | 4096 | 128 | 2048 |
| C | 512 | 8192 | 1024 | ≥8192 |
| D | 256 | 2048 | 512 | 4096 |
| E | 16 | 1024 | 256 | 4096 |
| F | 64 | 8192 | 2048 | 16384 |
| G | 128 | 2048 | 1024 | 4096 |
| H | 16 | 1024 | 1024 | 4096 |
| I | 64 | 4096 | 128 | 2048 |
| J | 64 | 32 | 256 | 1024 |

With one exception, therefore, the addition of IC31 improved titers.

The 936-10A-10A and 936-9C-10A polypeptides were confirmed to be fully adsorbed in the Al—H+IC31 formulations.

In further work the 936-10A-10A polypeptide was formulated with Al—H in a composition including 9 mg/ml NaCl and 10 mM histidine, pH 6.5. Water for injection and histidine buffer were mixed, and then NaCl was added to give a final osmolality of 308 mOsm/kg. Al—H was added to give a final Al$^{+++}$ concentration of 3 mg/ml. The polypeptide was added to give a final concentration of 100 µg/ml, left for 15 minutes under stirring at room temperature, and then stored overnight at 4° C. Just before administration, IC31 (with a 25:1 molar ratio of peptide:DNA, 1 µmol peptide) was added as an aqueous suspension, mixing equal volumes. The final mixture was isotonic and at physiological pH. Polypeptide adsorption was >90% (similar to the level seen with the Al—H alone).

Animals (6-week-old CD1 female mice), 8 per group, received 20 µg adjuvanted polypeptide intraperitoneally at day 0, with booster doses at days 21 & 35. Blood samples for analysis were taken on day 49 and were analysed by bactericidal assay, in the presence of rabbit or human complement, against a panel of 11 meningococcal strains. Titers were as follows:

|   | Rabbit complement | Human complement |
|---|---|---|
| A | 16384 | 1024 |
| B | 2048 | 512 |
| C | 4096 | >512 |
| D | 4096 | 256 |
| E | 4096 | 256 |
| F | 8192 | 64 |
| G | 4096 | 256 |
| H | 1024* | 256 |
| I | 4096 | — |
| J | 1024 | 256 |
| K | — | 512 |

*= bacteriostatic titer

Similar results were seen whether the 936-10A-10A polypeptide did or did not have a C-terminus hexahistidine tag (SEQ ID NOs: 18 vs. 24).

The 936-10A-10A polypeptide was substituted for the '936-741' polypeptide from 5CVMB, to give a mixture of three polypeptides having amino acid sequences of SEQ ID NOs: 13, 15 and 18/24. Bactericidal titers were similar, with a slight superiority when using the polypeptide without a histidine tag.

Compared to Al—H alone, IC31 alone, or MF59, the Al—H+IC31 mixture gave the best bactericidal strain coverage when using the 936-10A-10A polypeptide, either alone or in combination with other polypeptides from the 5CVMB mixture.

Meningococcus (iv)

The three polypeptides which make up the '5CVMB' vaccine disclosed in reference 31 were combined with a tetravalent mixture of meningococcal conjugates against serogroups A, C, W135 and Y. The mixture was adjuvanted with Al—H and/or IC31 (at high or low concentration). Bactericidal titers were as follows against a panel with one strain from each of serogroups A, C, W135 and Y:

|   | A | C | W135 | Y |
|---|---|---|---|---|
| Un-immunised | <16 | <16 | <16 | <16 |
| No adjuvant | 1024 | 256 | 128 | 512 |
| IC31$^{high}$ | 32768 | 16384 | 4096 | 4096 |
| IC31$^{low}$ | 16384 | 8192 | 1024 | 2048 |
| Al-hydroxide | 16384 | 8192 | 1024 | 4096 |
| Al—H + IC31$^{high}$ | 16384 | 32768 | 4096 | 8192 |
| Al—H + IC31$^{low}$ | 8192 | 65536 | 2048 | 8192 |

Thus the best titers against serogroups C, W135 and Y were seen when using a combination of aluminium hydroxide with IC31.

*E. coli*

The AcfD protein of *E. coli* (originally disclosed as SEQ ID NO: 3526 in reference 45; see also reference 44) is a useful immunogen. This antigen has been used to immunise mice in combination with various adjuvants, either alone or in combination. The immunised mice are then challenged with a lethal dose of *E. coli* and survival is assessed. Survival in control groups ranged from 0-25%, whereas survival after immunisation/challenge with adjuvanted AcfD was as follows:

| Adjuvant | Survival (10% ranges) |
| --- | --- |
| Freund's complete | 80-90% |
| Al—H | 70-80% |
| MF59 | 70-80% |
| IC31 | 70-80% |
| MF59 + IC31 | 80-90% |
| Al—H + IC31 | 100% |

Thus the best results were seen with the combination of Al—H and IC31.

Protection correlated with the reduction in bacterial load in the blood of infected animals.

It will be understood that the invention has been described by way of example only and modifications may be made whilst remaining within the scope and spirit of the invention.

REFERENCES

[1] *Vaccine Design: The Subunit and Adjuvant Approach* (Powell & Newman) 1995 (ISBN 0-306-44867-X).
[2] Clausi et al. (2008) *J Pharm Sci* DOI 10.1002/jps.21390
[3] Krieg (2003) *Nature Medicine* 9:831-835.
[4] McCluskie et al. (2002) *FEMS Immunology and Medical Microbiology* 32:179-185.
[5] WO98/40100.
[6] U.S. Pat. No. 6,207,646.
[7] U.S. Pat. No. 6,239,116.
[8] U.S. Pat. No. 6,429,199.
[9] WO01/93905.
[10] WO02/32451.
[11] Aichinger et al. (2008) *Cell Biology International* 32:1449-58.
[12] Alvarez-Bravo et al. (1994) *Biochem J* 302:535-8.
[13] Nakajima et al. (1997) *FEBS Letts* 415:64-66.
[14] Fritz et al. (2004) *Vaccine* 22:3274-84.
[15] Schellack et al. (2006) *Vaccine* 24:5461-72.
[16] Lingnau et al. (2007) *Expert Rev Vaccines* 6:741-6.
[17] WO2004/084938.
[18] Kamath et al. (2008) *Eur J Immunol* 38:1247-56.
[19] Riedl et al. (2008) *Vaccine* 26:3461-8.
[20] Kritsch et al. (2005) *J Chromatography B* 822:263-70.
[21] Lingnau et al. (2003) *Vaccine* 20:3498-508.
[22] Olafsdottir et al. (2009) *Scand J Immunol* 69:194-202.
[23] Hem & HogenEsch (2007) *Expert Rev Vaccines* 6:685-98.
[24] Gennaro (2000) *Remington: The Science and Practice of Pharmacy*. 20th edition, ISBN: 0683306472.
[25] Treanor et al. (1996) *J Infect Dis* 173:1467-70.
[26] Keitel et al. (1996) *Clin Diagn Lab Immunol* 3:507-10.
[27] WO03/097091.
[28] Cassone & Torosantucci (2006) *Expert Rev Vaccines* 5:859-67.
[29] PCT/IB2010/052445.
[30] PCT/IB2010/000998.
[31] Giuliani et al. (2006) *Proc Natl Acad Sci USA*. 103:10834-9.
[32] WO2004/084937.
[33] WO95/27787.
[34] WO03/010317.
[35] WO2007/110700.
[36] WO2006/138004.
[37] WO2005/084306.
[38] WO2005/002619.
[39] WO03/049762.
[40] WO02/02606.
[41] WO00/37494.
[42] WO2008/020330.
[43] WO2006/091517.
[44] WO/2009/104092.
[45] WO2006/089264.
[46] Covacci & Rappuoli (2000) *J. Exp. Med.* 19:587-592.
[47] WO 93/18150.
[48] Covacci et al. (1993) *Proc. Natl. Acad. Sci. USA* 90:5791-5795.
[49] Tummuru et al. (1994) *Infect. Immun.* 61:1799-1809.
[50] Marchetti et al. (1998) *Vaccine* 16:33-37.
[51] Telford et al. (1994) *J. Exp. Med.* 179:1653-1658.
[52] Evans et al. (1995) *Gene* 153:123-127.
[53] WO 96/01272 & WO96/01273, especially SEQ ID NO:6.
[54] WO 97/25429.
[55] *MMWR Morb Mortal Wkly Rep* 1998 Jan. 16; 47(1):12, 19.
[56] Harper et al. (2004) *Lancet* 364(9447):1757-65.
[57] U.S. Pat. No. 6,699,474.
[58] Tettelin et al. (2000) *Science* 287:1809-1815.
[59] WO00/66741.
[60] WO99/57280
[61] Martin et al. (1997) *J Exp Med* 185(7):1173-83.
[62] WO96/29412.
[63] Perkins-Balding et al. (2003) *Microbiology* 149:3423-35.
[64] WO01/55182.
[65] WO01/38350.
[66] WO00/23595.
[67] Masignani et al. (2003) *J Exp Med* 197:789-799.
[68] Welsch et al. (2004) *J Immunol* 172:5605-15.
[69] Hou et al. (2005) *J Infect Dis* 192(4):580-90.
[70] WO03/063766.
[71] Fletcher et al. (2004) *Infect Immun* 72:2088-2100.
[72] Zhu et al. (2005) *Infect Immun* 73(10):6838-45.
[73] WO2004/048404
[74] WO2006/024954.
[75] WO2007/060548.
[76] WO2004/032958.
[77] Ram et al. (2003) *J Biol Chem* 278:50853-62.
[78] WO98/53851
[79] U.S. Pat. No. 6,531,131.
[80] WO00/26384.
[81] U.S. Pat. No. 6,645,503.
[82] WO03/070282.
[83] WO94/08021
[84] WO2004/015099.
[85] WO2007/144316.
[86] WO2007/144317.
[87] WO02/09643.
[88] Katial et al. (2002) *Infect. Immun.* 70:702-707.
[89] U.S. Pat. No. 6,180,111.
[90] WO01/34642.

[91] WO2004/019977.
[92] EP-0011243.
[93] Fredriksen et al. (1991) NIPH Ann. 14(2):67-80.
[94] WO01/91788.
[95] WO2005/004908.
[96] Maiden et al. (1998) PNAS USA 95:3140-3145.
[97] WO98/56901.
[98] WO2006/081259.
[99] Claassen et al. (1996) 14(10):1001-8.
[100] WO99/10497.
[101] Steeghs et al. (2001) The EMBO Journal 20:6937-6945.
[102] WO01/52885.
[103] WO00/25811.
[104] WO01/09350.
[105] WO02/09746.
[106] WO02/062378.
[107] WO2004/014417.
[108] WO03/105890.
[109] WO2006/024946
[110] WO2009/081172.
[111] Seeber et al. (1991) J Parenteral Sci Technol 45:156-9.
[112] Kamath et al. (2008) PLoS ONE 3(11):e3683.
[113] WO2009/104097.

The invention claimed is:

1. An immunogenic composition comprising
   (i) an immunological adjuvant comprising an aluminium salt, an immunostimulatory oligonucleotide and a polycationic polymer, wherein the oligonucleotide and the polymer are associated with each other to form a complex; and
   (ii) a Neisserial immunogen which elicits a serum bactericidal immune response that protects against a Neisserial bacterial disease.

2. The composition of claim 1, wherein the aluminium salt is an aluminium hydroxide.

3. The composition of claim 1, wherein the aluminium salt is an aluminium phosphate.

4. The composition of claim 1, wherein the oligonucleotide is single-stranded and has between 10 and 100 nucleotides.

5. The composition of claim 4, wherein the oligonucleotide is 5'-(IC)$_{13}$-3'.

6. The composition of claim 1, wherein the polycationic polymer is a peptide.

7. The composition of claim 6, wherein the peptide includes one or more Leu-Leu dipeptide sequence(s), one or more Lys-Lys dipeptide sequence(s), and/or one or more Arg-Arg dipeptide sequence(s).

8. The composition of claim 6 or claim 7, wherein the peptide includes one or more Lys-Leu dipeptide sequence(s) and/or one or more Lys-Leu-Lys tripeptide sequence(s).

9. The composition of claim 6, wherein the peptide has between 5 and 50 amino acids.

10. The composition of claim 9, wherein the peptide has amino acid sequence KLKLLLLLKLK.

11. The composition of claim 1, wherein the oligonucleotide and polymer are present at a molar ratio 1:25.

12. The composition of claim 1, wherein the aluminium salt and the complex are both particulate with a mean particle diameter between 1-20 μm.

13. The composition of claim 1, wherein the adjuvant is sterile.

14. A process for preparing the composition of claim 13, comprising: filter sterilising an immunostimulatory oligonucleotide and a polycationic polymer; mixing the filter sterilised immunostimulatory oligonucleotide and a polycationic polymer under sterile conditions to form sterile complexes; mixing the sterile complexes with a sterile aluminium salt; and mixing the sterile adjuvant with sterile immunogen.

15. The composition of claim 1, wherein the immunogen is (a) adsorbed to the aluminium salt and/or (b) adsorbed to the complex.

16. A kit comprising: (i) a first container that contains an aluminium salt; and (ii) a second container that contains a complex of an immunostimulatory oligonucleotide and a polycationic polymer, wherein one or both of the first and second containers includes an immunogen.

17. The composition of claim 1, wherein the immunogen is from serogroup B meningococcus.

18. The composition of claim 1, wherein the immunogen is from *N. meningitidis*.

* * * * *